US009241493B2

(12) United States Patent
Jeschke et al.

(10) Patent No.: US 9,241,493 B2
(45) Date of Patent: Jan. 26, 2016

(54) USE OF AN ENAMINOCARBONYL COMPOUND IN COMBINATION WITH A BIOLOGICAL CONTROL AGENT

(75) Inventors: Peter Jeschke, Bergisch Gladbach (DE); Heike Hungenberg, Langenfeld (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 173 days.

(21) Appl. No.: 14/125,010

(22) PCT Filed: Jun. 12, 2012

(86) PCT No.: PCT/EP2012/061113
§ 371 (c)(1),
(2), (4) Date: Dec. 12, 2013

(87) PCT Pub. No.: WO2012/171914
PCT Pub. Date: Dec. 20, 2012

(65) Prior Publication Data
US 2014/0112899 A1   Apr. 24, 2014

Related U.S. Application Data

(60) Provisional application No. 61/497,240, filed on Jun. 15, 2011.

(30) Foreign Application Priority Data

Jun. 14, 2011  (EP) ................................... 11169732

(51) Int. Cl.
*A01N 63/00* (2006.01)
*A01N 25/00* (2006.01)
*A01N 43/40* (2006.01)
*A01N 63/02* (2006.01)
*A01N 63/04* (2006.01)

(52) U.S. Cl.
CPC ................ *A01N 63/00* (2013.01); *A01N 25/00* (2013.01); *A01N 43/40* (2013.01); *A01N 63/02* (2013.01); *A01N 63/04* (2013.01)

(58) Field of Classification Search
None
See application file for complete search history.

(56) References Cited

U.S. PATENT DOCUMENTS

| 4,186,195 A | 1/1980 | Yearian |
| 4,245,432 A | 1/1981 | Dannelly |
| 4,272,417 A | 6/1981 | Barke |
| 4,808,430 A | 2/1989 | Kouno |
| 5,023,183 A | 6/1991 | Friedman |
| 5,418,164 A | 5/1995 | Andersch |
| 5,804,208 A | 9/1998 | Andersch |
| 5,876,739 A | 3/1999 | Turnblad |
| 5,888,989 A | 3/1999 | Kern |
| 6,468,747 B1 | 10/2002 | De Beuckeleer |
| 6,994,849 B2 | 2/2006 | Droby |
| 8,105,979 B2 | 1/2012 | Hungenberg |
| 8,106,211 B2 | 1/2012 | Jeschke et al. |
| 8,110,528 B2 | 2/2012 | Hungenberg |
| 8,324,130 B2 | 12/2012 | Jeschke et al. |
| 8,404,855 B2 | 3/2013 | Jeschke et al. |
| 8,455,480 B2 | 6/2013 | Hungenberg |
| 8,497,228 B2 | 7/2013 | Hungenberg |
| 8,546,577 B2 | 10/2013 | Jeschke |
| 2001/0029014 A1 | 10/2001 | Beuckeleer |
| 2002/0102582 A1 | 8/2002 | Levine |
| 2002/0120964 A1 | 8/2002 | Rangwala |
| 2003/0097687 A1 | 5/2003 | Trolinder |
| 2003/0126634 A1 | 7/2003 | Spencer |
| 2003/0176428 A1 | 9/2003 | Schneidersmann |
| 2003/0188347 A1 | 10/2003 | Both |
| 2004/0172669 A1 | 9/2004 | Kraus |
| 2004/0250317 A1 | 12/2004 | Huber |
| 2005/0039226 A1 | 2/2005 | Barbour |
| 2005/0086719 A1 | 4/2005 | Spencer |
| 2005/0188434 A1 | 8/2005 | Spencer |
| 2005/0216969 A1 | 9/2005 | Song |
| 2006/0059581 A1 | 3/2006 | Spencer |
| 2006/0059590 A1 | 3/2006 | Cerny |
| 2006/0070139 A1 | 3/2006 | Bing |
| 2006/0095986 A1 | 5/2006 | Cavato |
| 2006/0130175 A1 | 6/2006 | Ellis |
| 2006/0162007 A1 | 7/2006 | Guo |
| 2006/0230473 A1 | 10/2006 | Johnson |
| 2006/0282915 A1 | 12/2006 | Malven |
| 2007/0028322 A1 | 2/2007 | Dizigan |
| 2007/0067868 A1 | 3/2007 | Negrotto |

(Continued)

FOREIGN PATENT DOCUMENTS

| EP | 0294053 | 12/1988 | |
| EP | 0539588 | 5/1993 | |
| EP | 0794704 | 9/1997 | |
| EP | 0268177 | 5/1998 | |
| EP | 1241247 | * 9/2002 | ............. C12N 1/20 |
| EP | 2201838 | 6/2010 | |
| WO | WO-8910396 | 11/1989 | |
| WO | WO-9425579 | 11/1994 | |
| WO | WO-9601563 | 1/1996 | |
| WO | WO-9616547 | 6/1996 | |

(Continued)

OTHER PUBLICATIONS

Deaker et al., Soil Bio. Biochem., 36:1275-1288 (2004).*

(Continued)

*Primary Examiner* — Blaine Lankford
*Assistant Examiner* — Thomas J Visone
(74) *Attorney, Agent, or Firm* — Miles & Stockbridge PC

(57) ABSTRACT

A combination comprising an enaminocarbonyl compound of formula (I): wherein R is methyl, cyclopropyl or 2,2-difluoroethyl, and at least one biological control agent selected from bacteria, fungi or yeasts, protozoas, viruses, and entomopathogenic nematodes, and optionally an inoculant, for reducing overall damage of plants and plant parts as well as losses in harvested fruits or vegetables caused by insects, mites nematodes and phytopathogens.

21 Claims, 1 Drawing Sheet

(56) References Cited

U.S. PATENT DOCUMENTS

| | | |
|---|---|---|
| 2007/0143876 A1 | 6/2007 | Song |
| 2007/0292854 A1 | 12/2007 | Behr |
| 2008/0028482 A1 | 1/2008 | Beazley |
| 2008/0064032 A1 | 3/2008 | Townshend |
| 2008/0070260 A1 | 3/2008 | Krieb |
| 2008/0167456 A1 | 7/2008 | Steiner |
| 2008/0196127 A1 | 8/2008 | De Beuckeleer |
| 2008/0260932 A1 | 10/2008 | Anderson |
| 2008/0280953 A1 | 11/2008 | Gorgens |
| 2008/0312082 A1 | 12/2008 | Kinney |
| 2008/0320616 A1 | 12/2008 | De Beuckeleer |
| 2009/0130071 A1 | 5/2009 | Gao |
| 2009/0137395 A1 | 5/2009 | Chicoine |
| 2009/0210970 A1 | 8/2009 | Hondred |
| 2009/0217423 A1 | 8/2009 | Cayley |
| 2009/0253749 A1 | 10/2009 | Jeschke et al. |
| 2009/0265817 A1 | 10/2009 | Weyens |
| 2009/0280981 A1 | 11/2009 | Jeschke et al. |
| 2009/0300784 A1 | 12/2009 | Long |
| 2010/0024077 A1 | 1/2010 | Cayley |
| 2010/0050282 A1 | 2/2010 | Trolinder |
| 2010/0056620 A1 | 3/2010 | Fishcer |
| 2010/0077501 A1 | 3/2010 | Trolinder |
| 2010/0080887 A1 | 4/2010 | Wagner |
| 2010/0167923 A1 | 7/2010 | Hungenberg et al. |
| 2010/0184079 A1 | 7/2010 | Cressman |
| 2010/0197494 A1 | 8/2010 | Hungenberg et al. |
| 2010/0197737 A1 | 8/2010 | Hungenberg |
| 2010/0210459 A1 | 8/2010 | Hungenberg et al. |
| 2010/0227762 A1 | 9/2010 | Hungenberg et al. |
| 2010/0298136 A1 | 11/2010 | Hungenberg |
| 2010/0298137 A1 | 11/2010 | Hungenberg |
| 2011/0033433 A1 | 2/2011 | Davies |
| 2011/0067141 A1 | 3/2011 | Froman |
| 2011/0110906 A1 | 5/2011 | Andersch |
| 2011/0138504 A1 | 6/2011 | Beazley |
| 2011/0300110 A1 | 12/2011 | Hungenberg |
| 2012/0157498 A1 | 6/2012 | Jeschke et al. |
| 2013/0123506 A1 | 5/2013 | Jeschke et al. |

FOREIGN PATENT DOCUMENTS

| | | |
|---|---|---|
| WO | WO-9633270 | 10/1996 |
| WO | WO-0026345 | 5/2000 |
| WO | WO-0026356 | 5/2000 |
| WO | WO-0131042 | 5/2001 |
| WO | WO-0141558 | 6/2001 |
| WO | WO-0151654 | 7/2001 |
| WO | 01/65944 | 9/2001 |
| WO | WO-0165944 | 9/2001 |
| WO | WO-0228186 | 4/2002 |
| WO | WO-0234946 | 5/2002 |
| WO | WO-0236831 | 5/2002 |
| WO | WO-0244407 | 6/2002 |
| WO | WO-0280675 | 10/2002 |
| WO | WO-02100163 | 12/2002 |
| WO | WO-03013224 | 2/2003 |
| WO | WO-03052073 | 6/2003 |
| WO | WO-2004011601 | 2/2004 |
| WO | WO-2004039986 | 5/2004 |
| WO | WO-2004053062 | 6/2004 |
| WO | WO-2004072235 | 8/2004 |
| WO | WO-2004074492 | 9/2004 |
| WO | WO-2004099447 | 11/2004 |
| WO | WO-2005054479 | 6/2005 |
| WO | WO-2005054480 | 6/2005 |
| WO | WO-2005059103 | 6/2005 |
| WO | WO-2005061720 | 7/2005 |
| WO | WO-2005103266 | 11/2005 |
| WO | WO-2005103301 | 11/2005 |
| WO | 2006/037475 | 4/2006 |
| WO | WO-2006037475 | 4/2006 |
| WO | WO-2006098952 | 9/2006 |
| WO | WO-2006108674 | 10/2006 |
| WO | WO-2006108675 | 10/2006 |
| WO | WO-2006128568 | 12/2006 |
| WO | WO-2006128569 | 12/2006 |
| WO | WO-2006128570 | 12/2006 |
| WO | WO-2006128571 | 12/2006 |
| WO | WO-2006128572 | 12/2006 |
| WO | WO-2006128573 | 12/2006 |
| WO | WO-2006130436 | 12/2006 |
| WO | WO-2007017186 | 2/2007 |
| WO | WO-2007024782 | 3/2007 |
| WO | WO-2007027777 | 7/2007 |
| WO | 2007/112842 | 10/2007 |
| WO | 2007/112843 | 10/2007 |
| WO | 2007/112845 | 10/2007 |
| WO | 2007/112847 | 10/2007 |
| WO | 2007/112848 | 10/2007 |
| WO | 2007/112894 | 10/2007 |
| WO | 2007/112895 | 10/2007 |
| WO | 2007/115644 | 10/2007 |
| WO | WO-2007112842 | 10/2007 |
| WO | WO-2007112843 | 10/2007 |
| WO | WO-2007112845 | 10/2007 |
| WO | WO-2007112847 | 10/2007 |
| WO | WO-2007112848 | 10/2007 |
| WO | WO-2007112894 | 10/2007 |
| WO | WO-2007112895 | 10/2007 |
| WO | WO-2007115644 | 10/2007 |
| WO | 2007/134778 | 11/2007 |
| WO | WO-2007134778 | 11/2007 |
| WO | 2007/144089 | 12/2007 |
| WO | WO-2007140256 | 12/2007 |
| WO | WO-2007142840 | 12/2007 |
| WO | WO-2007144089 | 12/2007 |
| WO | WO-2008002872 | 1/2008 |
| WO | WO-2008054747 | 5/2008 |
| WO | WO-2008112019 | 9/2008 |
| WO | WO-2008114282 | 9/2008 |
| WO | WO-2008122406 | 10/2008 |
| WO | 2009/030399 | 3/2009 |
| WO | WO-2009030399 | 3/2009 |
| WO | 2009/043442 | 4/2009 |
| WO | 2009/043443 | 4/2009 |
| WO | WO-2009043442 | 4/2009 |
| WO | WO-2009043443 | 4/2009 |
| WO | WO-2009064652 | 5/2009 |
| WO | WO-2009100188 | 8/2009 |
| WO | WO-2009102873 | 8/2009 |
| WO | WO-2009103049 | 8/2009 |
| WO | WO-2009111263 | 9/2009 |
| WO | 2009/124707 | 10/2009 |
| WO | WO-2009124707 | 10/2009 |
| WO | WO-2010024976 | 3/2010 |
| WO | WO-2010037016 | 4/2010 |
| WO | 2010/063382 | 6/2010 |
| WO | 2010/063465 | 6/2010 |
| WO | WO-2010063382 | 6/2010 |
| WO | WO-2010063465 | 6/2010 |
| WO | 2010/083955 | 7/2010 |
| WO | WO-2010077816 | 7/2010 |
| WO | WO-2010080829 | 7/2010 |
| WO | WO-2010083955 | 7/2010 |
| WO | WO-2010076212 | 9/2010 |
| WO | WO-2010117735 | 10/2010 |
| WO | WO-2010117737 | 10/2010 |
| WO | 2010/149369 | 12/2010 |
| WO | WO-2010149369 | 12/2010 |
| WO | WO-2011022469 | 2/2011 |
| WO | WO-2011034704 | 3/2011 |
| WO | WO-2011062904 | 5/2011 |
| WO | WO-2011066360 | 6/2011 |
| WO | WO-2011066384 | 6/2011 |
| WO | WO-2011075593 | 6/2011 |
| WO | WO-2011075595 | 6/2011 |
| WO | WO-2011084621 | 7/2011 |

OTHER PUBLICATIONS

"European Search Report for European Patent Application No. 11169732.2, dated Oct. 21, 2011", 1-7.

(56) References Cited

OTHER PUBLICATIONS

"International Search Report for International Application No. PCT/EP2010/000123, dated Jul. 6, 2011 (with english translation)", 1-14.
"International Search Report for International Application No. PCT/EP2012/061113, dated Aug. 14, 2012", 1-7.
Chen et al. (2007), Nature Biotechnol. 25(9): 1007-14.
Dulmage et al., 1971, J. Invertebrate Path. 18: 353-358.
Dutky et al. (1964), J. Insect Pathol. 6 : 417-422.
Fan et al., (2011), Journal of Biotechnology 151:303-311.
Flanders et al. (1996), J. Econ Entomol. 89: 373:380.
Jehle et al., (1992), Journal of general virology, 73: 1621-1626.
Koumoutsi et al. (2004), J. Bacteriol. 186: 1084-1096.
Krebs et al. (1998) J Plant Dis Prot 105:181-197.
Nanninga, The Journal of Cell Biology. vol. 48, 1971 pp. 219-224.
Rogoff et al., 1969, J. Invertebrate Path. 14: 122-129.
Simser (1992) J. of Nematology 24(3) pp. 374-378.
Tanada. (1964), J. Insect Pathol. 6: 378-380.
Wegler, "Chemistry of Crop Protection Agents and Pesticides", vol. 2, Springer Verlag, 1970, pp. 401-412.
International Search Report for PCT/EP2012/061113 Mailed Aug. 14, 2012.

* cited by examiner

Genealogy of Group 1 bacteria according to Ash et al., 1991
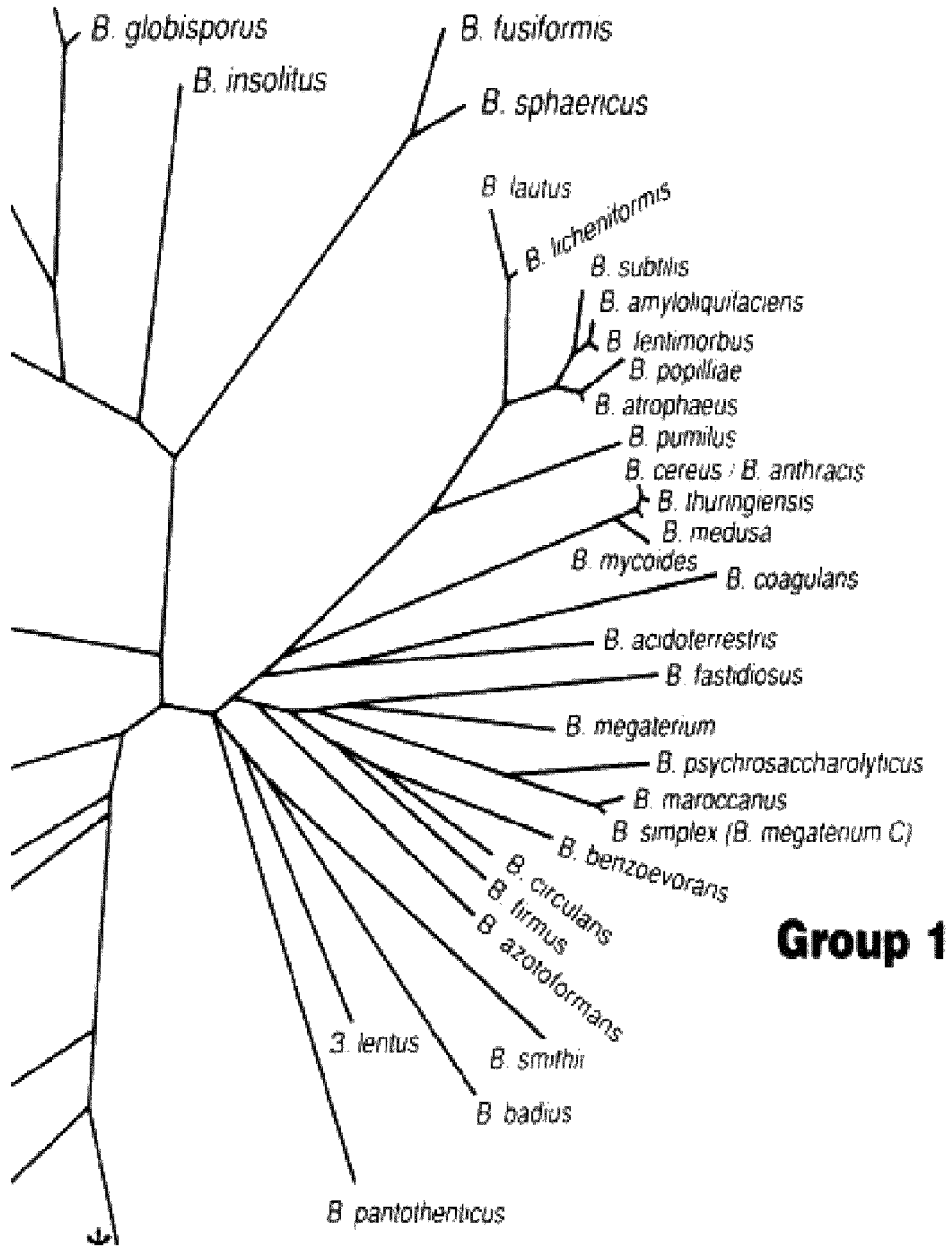

USE OF AN ENAMINOCARBONYL COMPOUND IN COMBINATION WITH A BIOLOGICAL CONTROL AGENT

CROSS REFERENCE TO RELATED APPLICATIONS

This application is a §371 National Stage Application of PCT/EP2012/061113, filed Jun. 12, 2012, which claims priority to European Application No. 11169732.2, filed Jun. 14, 2011, and claims benefit of U.S. Provisional Application No. 61/497,240, filed Jun. 15, 2011.

BACKGROUND OF THE INVENTION

1. Field of the Invention

The present invention relates to the use of an enaminocarbonyl compound in combination with a biological control agent as well as to a preparation method of compositions containing a selected enaminocarbonyl compound and a selected biological control agent, and compositions containing the enaminocarbonyl compound and at least one biological control agent.

2. Description of Related Art

From EP 0 539 588 and WO 2007/115644 it is known that certain enaminocarbonyl compounds are useful for combating harmful pests which occur in the agriculture. Several methods to apply such compounds are described therein. WO 2006/037475 describes in particular the treatment of seed with specific enaminocarbonyl compounds. Binary combinations containing a specific enaminocarbonyl compound and a specific insecticide or fungicide have been described in several international patent publications (cf. WO 2007/112848, WO 2007/112845, WO 2007/112843, WO 2007/112842, WO 2007/112847, WO 2007/112895, WO 2007/112894, WO 2007/134778, WO 2009/030399, WO 2009/043443, WO 2009/043442, WO 2010/063465). For some of the mixtures disclosed therein, it has been shown by way of experiments that a synergistic activity increase occurs by combining the specific active ingredients. The known prior art combinations, however, just combine two chemical ingredients (agrochemicals).

However, environmental and economic requirements imposed in modern-day crop protection agents are continually increasing. This is particularly true with regard to the spectrum of action, toxicity, selectivity, application rate, and formation of residues. Additionally, when applying agrochemicals, there are always the problems with resistances. Thus, there is a constant need for developing new, alternative plant protection agents which in some areas at least help to fulfill the abovementioned requirements. Moreover, there is a constant need to develop novel plant treatment agents which are particularly environmentally friendly. Also, as concerns regarding a possible impact of agrochemicals on the environment and the health of humans and animals are growing in the public opinion, efforts have to be made to reduce the amount of agrochemicals applied.

SUMMARY

The inventors now surprisingly found that specific enaminocarbonyl compounds can be combined with selected biological control agents and thus satisfying above mentioned needs. The inventors even found that a synergistic activity increase occurs by combining selected enaminocarbonyl compounds with selected biological control agents.

The particular enaminocarbonyl compounds which can be used in combination with at least one biological control agent selected from bacteria, in particular spore-forming bacteria, fungi or yeasts, protozoas, viruses, and entomopathogenic nematodes, optionally in the presence of inoculants have the formula (I)

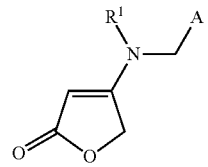

in which
R$^1$ represents alkyl, haloalkyl, alkenyl, haloalkenyl, alkynyl, cycloalkyl, cycloalkylalkyl, halocycloalkyl, alkoxy, alkoxyalkyl or halocycloalkylalkyl; and
A represents pyrid-2-yl or pyrid 4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl, or represents a radical pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine), or represents a radical

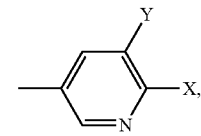

in which
X represents halogen, alkyl or haloalkyl,
Y represents halogen, alkyl, haloalkyl, haloalkoxy, azido or cyano.

BRIEF DESCRIPTION OF THE DRAWINGS

FIG. 1 represents embodiments described herein.

DETAILED DESCRIPTION OF A PREFERRED EMBODIMENT

Preferred enaminocarbonyl compounds of formula (I) are compounds of the formula (IA)

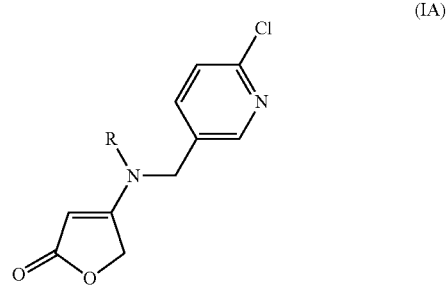

wherein R is methyl, cyclopropyl or 2,2-difluoroethyl,
i.e. in particular enaminocarbonyl compound (I-1), namely 4-{[(6-Chloropyrid-3-yl)methyl](methyl)amino}furan-2 (5H)-one, compound (I-2), namely 4-{[(6-Chloropyrid-3-yl) methyl](cyclopropyl)amino}furan-2(5H)-one, or compound (I-3), namely 4-{[(6-Chloropyrid-3-yl)methyl](2,2-difluoroethyl)amino}furan-2(5H)-one having the following formulae

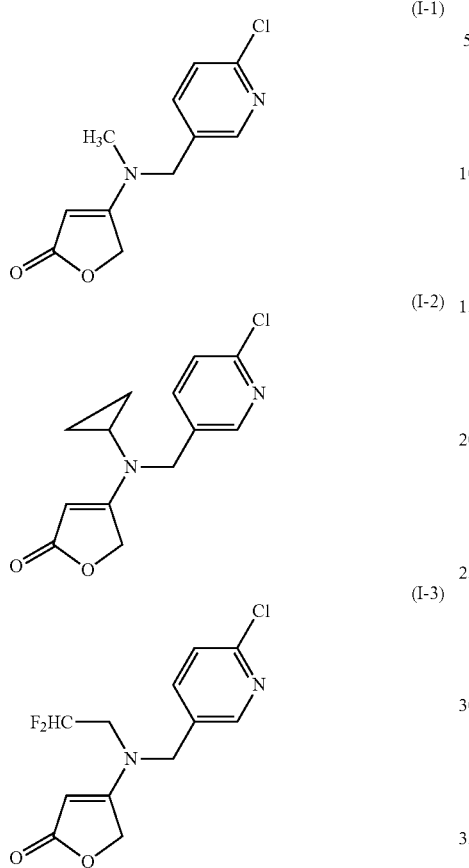

The compounds of formula (I) in combination with at least one biological control agent selected from bacteria, in particular spore-forming bacteria, fungi or yeasts, protozoas, viruses, and entomopathogenic nematodes, optionally in the presence of inoculants, are suitable for reducing overall damage of plants and plant parts as well as losses in harvested fruits or vegetables caused by insects, mites, nematodes and phytopathogens.

The compound of formula (I-3) is particularly preferred to be used or employed according to the invention, thus, also if not mentioned explicitly, the naming of a compound (I-1), (I-2) or (I-3) always implies that the compound of formula (I-3) is preferred. According to the invention, the biological control agent may be employed or used in any physiologic state such as active or dormant. Dormant yeast e.g. may be supplied for example frozen, dried, or lyophilized.

Thus, a first aspect of the present invention refers to a combination comprising an enaminocarbonyl compound of formula (IA):

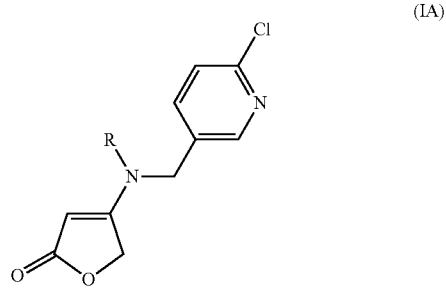

wherein the compound of formula (IA) is a compound selected from compound (I-1), (I-2) or (I-3) having the following formulae

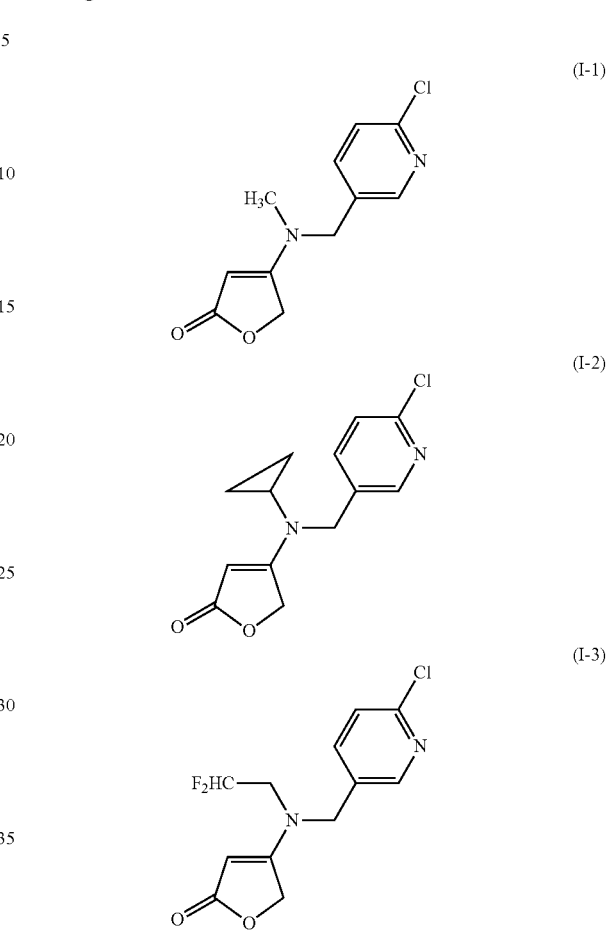

and at least one biological control agent selected from bacteria, fungi or yeasts, protozoas, viruses, and entomopathogenic nematodes, and optionally an inoculant. This combination is suitable for reducing overall damage of plants and plant parts as well as losses in harvested fruits or vegetables caused by insects, mites, nematodes and phytopathogens.

One preferred embodiment refers to a combination according to the invention wherein the biological control agent is selected from the group consisting of bacteria, fungi, yeasts or viruses.

Another preferred embodiment refers to a combination according to the invention, wherein the inoculant is selected from a group consisting of bacteria of the genus *Rhizobium leguminosarum, Rhizobium tropici, Rhizobium loti, Rhizobium trifolii, Rhizobium meliloti, Rhizobium fredii, Azorhizobium caulinodans, Pseudomonas, Azospirillum, Azotobacter, Streptomyces, Burkholdia, Agrobacterium, Endo-, Ecto-*, and *Vesicular-Arbuscular Mycorhizza*.

Yet another preferred embodiment refers to a combination according to the invention, wherein the biological control agent is selected from a group consisting of *Metschnikowia fructicola, Bacillus subtilis, Bacillus thuringiensis, Paecilomyces lilacinu, Bacillus amyloliquefaciens, Cydia pomonella Granulosis virus*, and *Metarhizium anisopliae*.

Moreover, another aspect refers to the use of an enaminocarbonyl compound (I-1), (I-2) or (I-3) in combination with at least one biological control agent selected from bacteria, fungi or yeasts, protozoas, viruses, and entomopathogenic nematodes, optionally in the presence of inoculants, for reducing overall damage of plants and plant parts as well as losses in harvested fruits or vegetables caused by insects, mites, nematodes and phytopathogens. Preferably, the plant part is a seed or a plant emerging from the seed, wherein the seed is from a conventional or a transgenic plant.

Yet another preferred embodiment refers to said use wherein the plant is a horticultural crop selected from carrots, pumpkin, squash, zucchini, potato, sweet corn, onions, ornamentals, medicinal herbs, culinary herbs, tomatoes, spinach, pepper, melon, lettuce, cucumber, celery, beets, cabbage, cauliflower, broccoli, Brussels sprouts, turnip cabbage, kale, radish, rutabaga, turnip, asparagus, bean, pea, apples, raspberry, strawberry, banana, mango, grapes, peaches, pears, guava, pineapple, pomegranate, garlic, *capsicum*, chili, radish, star fruit, tapioca, walnuts, lemon, mandarin, mangold, mushroom, olive, orange, papaya, paprika, passion fruit, peanuts, pecan nuts, prune, pistachio nuts, persimmon, pamplemouse (grapefruit), eggplant, endive, cranberry, gooseberry, hazel nuts, kiwifruit, almonds, amaranth, apricot, artichoke, avocado, blackberry, cashew nut, cherry, clementine, coconut, and cantaloupes, preferably the plant is a broad acre crop selected from cotton, corn, soybean, cereals, canola, oil seed rape, sugar cane and rice.

A third aspect refers to a method for reducing overall damage of plants and plant parts as well as losses in harvested fruits or vegetables caused by insects mites, nematodes and/or phytopathogens comprising the step of simultaneously or sequentially applying a compound (I-1), (I-2) or (I-3) and at least one biological control agent selected from bacteria, fungi or yeasts, protozoas, viruses, and entomopathogenic nematodes and optionally at least an inoculant on the plant, plant parts, harvested fruits or vegetables.

One preferred embodiment refers to said method, wherein the plant part is a seed or a plant emerging from the seed. The seed can be from a conventional or a transgenic plant.

Another preferred embodiment refers to said method, wherein the plant is a horticultural crop selected from carrots, pumpkin, squash, zucchini, potato, sweet corn, onions, ornamentals, medicinal herbs, culinary herbs, tomatoes, spinach, pepper, melon, lettuce, cucumber, celery, beets, cabbage, cauliflower, broccoli, Brussels sprouts, kohlrabi, kale, radish, rutabaga, turnip, asparagus, bean, pea, apples, raspberry, strawbeny, banana, mango, grapes, peaches, pears, guava, pineapple, pomegranate, garlic, *capsicum*, chili, radish, star fruit, tapioca, walnuts, lemon, mandarin, mangold, mushroom, olive, orange, papaya, paprika, passion fruit, peanuts, pecan nuts, prune, pistachio nuts, persimmon, pamplemouse (grapefruit), eggplant, endive, cranberry, gooseberry, hazel nuts, kiwifruit, almonds, amaranth, apricot, artichoke, avocado, blackberry, cashew nut, cherry, clementine, coconut, and cantaloupes preferably the plant is a broad acre crop selected from cotton, corn, soybean, cereals, canola, oil seed rape, sugar cane and rice.

Another aspect refers to a formulation comprising a compound of formula (IA) as defined in claim 1 and at least one biological control agent selected from bacteria, fungi or yeasts, protozoas, viruses, and entomopathogenic nematodes as described herein.

The invention is further directed to the preparation of a composition containing a compound (I-1), (I-2) or (I-3) and at least one biological control agent selected from bacteria, in particular spore-forming bacteria, fungi or yeasts, protozoas, viruses, and entomopathogenic nematodes, and optionally an inoculant, for reducing overall damage of plants and plant parts as well as losses in harvested fruits or vegetables caused by insects, mites, nematodes and phytopathogens.

The invention is also directed to the use of a compound (I-1), (I-2) or (I-3) and at least one biological control agent selected from bacteria, in particular spore-forming bacteria, fungi or yeasts, protozoas, viruses, and entomopathogenic nematodes, and optionally at least an inoculant, for the treatment of seeds or a plant emerging from the seed.

Moreover the invention is directed to a method for protecting seeds comprising the step of simultaneously or sequentially applying a compound (I-1), (I-2) or (I-3) and at least one biological control agent selected from bacteria, in particular spore-forming bacteria, fungi or yeasts, protozoas, viruses, and entomopathogenic nematodes, and optionally at least an inoculant, on a seed or a plant emerging from the seed. The method is further called "seed treatment".

The compound (I-1), (I-2) or (I-3) and the biological control agent selected from bacteria, in particular spore-forming bacteria, fungi or yeasts, protozoas, viruses, and entomopathogenic nematodes, and optionally an inoculant may be applied in any desired manner, such as in the form of a seed coaling, soil drench, and/or directly in-furrow and/or as a foliar spray and applied either pre-emergence, post-emergence or both. In other words, the composition can be applied to the seed, the plant or to harvested fruits and vegetables or to the soil wherein the plant is growing or wherein it is desired to grow.

Reducing the overall damage of plants and plant parts often results in healthier plants and/or in an increase in plant vigor and/or yield. For example, the yield of plants treated according to the invention is at least 1%, 2%, 3%, 4%, 5%, 6%, 7%, 8%, 9%, 10% higher than the yield of untreated plants when grown under the same environmental conditions.

The use or the method to use a compound (I-1), (I-2) or (I-3) and at least one biological control agent selected from bacteria, in particular spore-forming bacteria, fungi or yeasts, protozoas, viruses, and entomopathogenic nematodes simultaneously or sequentially includes the following application methods, namely both above mentioned components may be formulated into a single, stable composition with an agriculturally acceptable shelf life (so called "solo-formulation"), or being combined before or at the time of use (so called "combined-formulations"), If not mentioned otherwise, the expression "combination" stands for the various combinations of the compound (I-1), (I-2) or (I-3) and the biological control agent selected from bacteria, in particular spore-forming bacteria, fungi or yeasts, protozoas, viruses, and entomopathogenic nematodes, and optionally the inoculant, in a solo-formulation, in a single "ready-mix" form, in a combined spray combination composed from solo-formulations, such as a "tank-mix", and especially in a combined use of the single active ingredients when applied in a sequential manner, i.e. one after the other within a reasonably short period, such as a few hours or days, e.g. 2 hours to 7 days. The order of applying compound (I-1), (I-2) or (I-3) and the biological control agent selected from bacteria, in particular spore-forming bacteria, fungi or yeasts, protozoas, viruses, and entomopathogenic nematodes and optionally the inoculant, is not essential for working the present invention. Accordingly, the term "combination" also encompasses the presence of the compound (I-1), (I-2) or (I-3) and the biological control agent selected from bacteria, in particular spore-forming bacteria, fungi or yeasts, protozoas, viruses, and entomopathogenic nematodes on or in a plant to be treated or its surrounding, habitat or storage space, e.g. after simultaneously or consecutively applying compound (I-1), (I-2) or (I-3) and the biological control agent selected from bacteria, in particular spore-forming bacteria, fungi or yeasts, protozoas, viruses, and entomopathogenic nematodes to a plant its surrounding, habitat or storage space.

If the compounds (I-1), (I-2) or (I-3) and the biological control agent selected from bacteria, in particular spore-forming bacteria, fungi or yeasts, protozoas, viruses, and entomopathogenic nematodes and optionally an inoculant, are employed or used in a sequential manner, it is preferred to treat the plants or plant parts (which includes seeds and plants emerging from the seed), harvested fruits and vegetables according to the following method: Firstly applying the compound (I-1), (I-2) or (I-3) on the plant or plant parts, and secondly applying the biological control agent selected from bacteria, in particular spore-forming bacteria, fungi or yeasts, protozoas, viruses, and entomopathogenic nematodes and optionally the inoculant, to the same plant or plant parts. The time periods between the first and the second application within a (crop) growing cycle may vary and depend on the effect to be achieved. For example, the first application is done to prevent an infestation of the plant or plant parts with insects, mites, nematodes and/or phytopathogens (this is particularly the case when treating seeds) or to combat the infestation with insects, mites, nematodes and/or phytopathogens (this is particularly the case when treating plants and plant parts) and the second application is done to prevent or control the infestation with insects, mites, nematodes and/or phytopathogens. Control in this context means that the biological control agent is not able to fully exterminate the pests or phytopathogenic fungi but is able to keep the infestation on an acceptable level.

By following the before mentioned steps, a very low level of residues of the compound (I-1), (I-2) or (I-3) on the treated plant, plant parts, and the harvested fruits and vegetables can be achieved.

If not mentioned otherwise the treatment of plants or plant parts (which includes seeds and plants emerging from the seed), harvested fruits and vegetables with the compound (I-1), (I-2) or (I-3), preferably compound (I-3), and the biological control agent selected from bacteria, in particular spore-forming bacteria, fungi or yeasts, protozoas, viruses, and entomopathogenic nematodes, and optionally the inoculant, is carried out directly or by action on their surroundings, habitat or storage space using customary treatment methods, for example dipping, spraying, atomizing, irrigating, evaporating, dusting, fogging, broadcasting, foaming, painting, spreading-on, watering (drenching), drip irrigating. It is furthermore possible to apply the compound (I-1), (I-2) or (I-3), preferably compound (I-3), and the biological control agent selected from bacteria, in particular spore-forming bacteria, fungi or yeasts, protozoas, viruses, and entomopathogenic nematodes, and optionally the inoculant, as solo-formulation or combined-formulations by the ultra-low volume method, or to inject the compound (I-1), (I-2) or (I-3), preferably compound (I-3), and the biological control agent selected from bacteria, in particular spore-forming bacteria, fungi or yeasts, protozoas, viruses, and entomopathogenic nematodes, and optionally the inoculant, as a composition or as sole-formulations into the soil (in-furrow).

In general, the terms "spore-forming bacteria", "fungi" or "yeasts" comprise spores and other inactive forms of said organisms which can yield in active organisms. Thus, in one embodiment, said organisms are comprised in form of spores in a formulation, e.g., a solo- or combined-formulation.

In general, the term "nematode" comprises eggs, larvae, juvenile and mature forms of said organism. Thus, in one embodiment, said organisms are comprised in form of eggs, larvae, juvenile or mature form in a formulation, e.g., a solo- or combined-formulation.

A solo- or combined-formulation is the formulation which is applied to the plants to be treated (e.g., in a greenhouse, on a field, in a wood), e.g., a tank formulation comprising the biological control agent in accordance with the present invention and a compound (I-1), (I-2) or (I-3) or a liquid or solid formulation comprising said biological control agent which is applied prior, after or in parallel with a compound (I-1), (I-2) or (I-3) to a plant to be treated.

The term "plant to be treated" encompasses every part of a plant including its root system and the material—e.g., soil or nutrition medium—which is in a radius of at least 10 cm, 20 cm, 30 cm around the caulis or bole of a plant to be treated or which is at least 10 cm, 20 cm, 30 cm around the root system of said plant to be treated, respectively.

In the case of seed treatment, the treatment can be carried out by applying the compound (I-1), (I-2) or (I-3), preferably compound (I-3), and the biological control agent selected from bacteria, in particular spore-forming bacteria, fungi or yeasts, protozoas, viruses, and entomopathogenic nematodes, and optionally the inoculant, as a solution, a powder (for dry seed treatment), a water-soluble powder (for slurry seed treatment), or by incrusting, by coating with one or more layers containing the compound (I-1), (I-2) or (I-3), preferably compound (I-3), and the biological control agent selected from bacteria, in particular spore-forming bacteria, fungi or yeasts, protozoas, viruses, and entomopathogenic nematodes, and optionally the inoculant.

As already mentioned before, using a compound (I-1), (I-2) or (I-3) and at least one biological control agent selected from bacteria, in particular spore-forming bacteria, fungi or yeasts, protozoas, viruses, and entomopathogenic nematodes and optionally an inoculant, as a combination is advantageous. The broadening of the activity spectrum to other agricultural pests (i.e. insects, acari, nematodes, and phytopathogens) and, for example to resistant strains of such agricultural pests and/or plant diseases can be achieved.

Also according to the invention, the compound (I-1), (I-2) or (I-3) and the biological control agent selected from bacteria, in particular spore-forming bacteria, fungi or yeasts, protozoas, viruses, and entomopathogenic nematodes can be used in a lower application rate and still achieve the sufficient control of the agricultural pests and/or plant diseases. This is particularly visible if application rates for the before mentioned compounds or biological control agents are used where the individual compounds or biological control agents show no or virtually no activity. The invention can also result in an advantageous behavior during formulation or during use, for example during grinding, sieving, emulsifying, dissolving or dispensing; improved storage stability and light stability, advantageous residue formation, improved toxicological or ecotoxicological behaviour, improved properties of the plant, for example better growth, increased harvest yields, a better developed root system, a larger leaf area, greener leaves, stronger shoots, less seed required, lower phytotoxicity, mobilization of the defense system of the plant, good compatibility with plants. Moreover, even an enhanced systemic action of the compound (I-1), (I-2) or (I-3) or the biological control agent selected from bacteria, in particular spore-forming bacteria, fungi or yeasts, protozoas, viruses, and entomopathogenic nematodes is higher and/or a persistency of the fungicidal, insecticidal, acaricidal and/or nematicidal action is expected.

Using a compound (I-1), (I-2) or (I-3) and at least one biological control agent selected from bacteria, in particular spore-forming bacteria, fungi or yeasts, protozoas, viruses, and entonaopathogenic nematodes and optionally an inoculant, as a combination is particularly suitable for treating seed. A large part of the damage to crop plants caused by harmful agricultural pests and/or plant diseases is triggered by an infection of the seed during storage or after sowing as well as during and after germination of the plant. This phase is particularly critical since the roots and shoots of the growing plant are particularly sensitive, and even small damage may result in a weak plant (unhealthy plant), reduced yield and even in the death of the plant.

The control of pests and/or phytopathogens by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or which at least considerably reduce additional application. It is furthermore desirable to optimize the amount of agrochemicals employed in such a way as to provide maximum protection for the seed and the germinating plant from attack by agricultural pests, but without damaging the plant itself by the active compound employed. In particular, methods for the treatment of seed should also take into consideration the intrinsic insecticidal properties of plants in order to achieve optimum protection of the seed and the germinating plant with a minimum of agrochemicals being employed.

As already mentioned, the compound (I-1), (I-2) or (I-3) and the biological control agent selected from bacteria, in particular spore-forming bacteria, fungi or yeasts, protozoas, viruses, and entomopathogenic nematodes and optionally an inoculant can be employed or used according to the invention as a solo- or a combined-formulation. Such formulations may include agriculturally suitable auxiliaries, solvents, carriers, surfactants and/or extenders.

According to the invention, biological control agents which are summarized under the term "bacteria" include spore-forming, root-colonizing bacteria, or bacteria useful as bioinsecticide biofungicide and/or bionematicide. Examples of such bacteria to be used or employed according to the invention are:

(1.1) *Bacillus agri*, (1.2) *Bacillus aizawai*, (1.3) *Bacillus albolactis*, (1.4) *Bacillus amyloliquefaciens*, in particular the strain IN937a, or strain FZB42 (DSM 23117, BGSC 10A6, product known as RhizoVital®), (1.5) *Bacillus cereus*, in particular spores of *Bacillus cereus* strain CNCM I-1562 (cf. U.S. Pat. No. 6,406,690), (1.6) *Bacillus coagulans*, (1.7) *Bacillus endoparasiticus*, (1.8) *Bacillus endorhythmos*, (1.9) *Bacillus azotoformans*, (1.10) *Bacillus kurstaki*, (1.11) *Bacillus lacticola*, (1.12) *Bacillus lactimorbus*, (1.13) *Bacillus lactis*, (1.14) *Bacillus laterosporus*, (1.15) *Bacillus lentimorbus*, (1.16) *Bacillus licheniformis*, (1.17) *Bacillus medusa*, (1.18) *Bacillus megaterium*, (1.19) *Bacillus metiens*, (1.20) *Bacillus natto*, (1.21) *Bacillus nigrificans*, (1.22) *Bacillus pupillae*, (1.23) *Bacillus pumilus*, in particular strain GB34 (ATCC 700814, products known as Yield Shield®) and strain QST2808 (NRRL No. B-30087, products known as Sonata QST 2808®), (1.24) *Bacillus siamensis*, (1.25) *Bacillus sphaericus* (products known as VectoLexs®, (1.26) *Bacillus subtilis*, in particular strain GB03 (ATCC SD-1397, products known as Kodiak®) and strain QST713 (NRRL No. B-21661, products known as Serenade QST 713®), or *Bacillus subtilis* var. *amyloliquefaciens* strain FZB24 (products known as Taegro®), (1.27) *Bacillus thuringiensis*, in particular *Bacillus thuringiensis* var. *israelensis* (products known as VectoBac®) or *Bacillus thuringiensis* subsp. *aizawai* strain ABTS-1857 (products known as XenTari®), or *Bacillus thuringiensis* subsp. *kurstaki* strain HD-1 (products known as Dipel® ES) or *Bacillus thuringiensis* subsp. *tenebrionis* strain NB 176 (products known as Novodor® FC), (1.28) *Bacillus uniflagellatus*, (1.29) *Delftia acidovorans*, in particular strain RAY209 (products known as BioBoost®), (1.30) *Lysobacter antibioticus*, in particular strain 13-1 (cf. Biological Control 2008, 45, 288-296), (1.31) *Pasteuria penetrans*, (1.32) *Pseudomonas chlororaphis*, in particular strain MA 342 (products known as Cedomon), (1.33) *Pseudomonas proradix* (products known as Proradix®), (1.34) *Streptomyces galbus*, in particular strain K61 (products known as Mycostop®, cf. Crop Protection 2006, 25, 468-475), (1.35) *Streptomyces griseoviridis* (products known as Mycostop®), (1.36) *Bacillus lautus*, (1.37) *Bacillus atrophaeus*, (1.38) *Bacillus anthracis*, (1.39) *Bacillus mycoides*, (1.40) *Bacillus acidoterrestris*, (1.41) *Bacillus fastidiosus*, (1.42) *Bacillus psychrosaccharolyticus*, (1.43) *Bacillus maroccanus*, (1.44) *Bacillus megaterium* C, (1.45) *Bacillus pantothenticus*, (1.46) *Bacillus lentus*, (1.47) *Bacillus badius*, and (1.48) *Bacillus smithi*.

*Bacillus* (abbreviation: B.) is a genus of rod-shaped, gram-positive bacteria, which can produce endospores under stressful environmental conditions. The single species of this genus differ strongly with respect to their usability in the area of plant protection. In contrast, *Bacillus subtilis*, for example the strains GB03 and QST 713, as well as *Bacillus amyloliquefaciens*, strain FZB 42, are species with phytopathogenic properties. These bacteria are applied to the soil and/or to the leaves.

On the other hand *Bacillus thuringiensis* with its different subspecies *produces* endotoxin containing crystals which have high insect pathogenic specifity. *Bacillus thuringiensis* subsp. *kurstaki*, strain HD-1, is used for control of lepidopteran larvae, but without noctuidae. *Bacillus thuringiensis* subsp. *aizawai*, for example the strains SAN 401 I, ABG-6305 and ABG-6346, is effective against different lepidopteran species including also noctuidae. *Bacillus thuringiensis* subsp. *tenebrionis*, for example the strains SAN 418 I and ABG-6479, protects plants against leaf beetle larvae. *Bacillus thuringiensis* subsp. *israelensis*, for example the strains SAN 402 I and ABG-6164, is applied against larvae of various dipteran pests, e.g. mosquitoes and nematoceres.

From the given bacteria (1.1) to (1.48), such bacteria or mutants thereof that have an insecticidal or plant growth promoting activity are preferred to be used or employed in the present invention, in one embodiment in combination with compound (I-3), optionally in the presence of an inoculant.

From the given bacteria (1.1) to (1.48), such bacteria or mutants thereof that have a fungicidal activity are preferred to be used or employed in the present invention, in one embodiment in combination with compound (I-3), optionally in the presence of an inoculant.

In one embodiment, from the given bacteria (1.1) to (1.48), the bacteria given under the numbers (1.4), (1.5), (1.6), (1.15), (1.16), (1.17), (1.22), (1.23), (1.26), (1.27) and (1.36) to (1.44) are to be used or employed in the present invention, such as in combination with compound (I-3), optionally in the presence of an inoculant. These bacteria belong to the class of group 1 bacteria as disclosed in Ash et al., 1991, Lett Appl Microbiology 13, 202-206. The genealogy of group 1 bacteria is also shown in FIG. 1. Notably, Group 1 bacteria can be divided into subgroups depending on the ramification within the group. Thus, subgroup (1) consists of *B. pantothenticus, B, lentus, B. badius,* and *B. smithi;* subgroup (2) consists of *B. azotoformans, B. firmus, B. circulans, B. benzoevorans, B. simplex, B. marrocanus, B. psychrosaccharolyticus, B. megaterium* and *B. fastidiosus;* and subgroup (3) consists of *B. lautus, B. licheniformis, B. subtilis, B. amyloliquifaciens, B. lentimorbus, B. popilliae, B. atrophaeus, B. pumilus, B. cereus, B. anthracia, B. thuringiensis, B. medusa, B. mycoides, B. coagulans,* and *B. acidoterrestris.* Subgroup (3) can be further divided into subgroup (3a) consisting of *B. lautus, B. licheniformis, B. subtilis, B. amyloliquifaciens, B. lentimorbus, B. popilliae,* and *B. atrophaeus;* subgroup (3b) consisting of *B. pumilus, B. cereus, B. thuringiensis, B. medusa,* and *B. mycoides;* and subgroup (3c) consisting of *B. coagulans,* and *B. acidoterrestris.*

In one embodiment, the bacteria of subgroup (3), (3a), (3b) or (3c) are to be used or employed in the present invention, such as in combination with compound (I-3), optionally in the presence of an inoculant.

In another embodiment, the bacteria of subgroup (1) are to be used or employed in the present invention, such as in combination with compound (I-3), optionally in the presence of an inoculant.

In another embodiment, the bacteria given under the numbers (1.4), (1.5), (1.23), and (1.26) are to be used or employed in the present invention, such as in combination with compound (I-3), optionally in the presence of an inoculant.

From the given bacteria (1.4), the bacteria (1.4a) *Bacillus amyloliquefaciens* strain IN937a, and (1.4b) *Bacillus amyloliquefaciens* strain FZB42 are used or employed in the present invention, in one embodiment in combination with compound (I-3), optionally in the presence of an inoculant.

From the given bacteria (1.5), the bacterium (1.5a) *Bacillus cereus* strain CNCM I-1562 especially spores are used or employed in the present invention, in one embodiment in combination with compound (I-3), optionally in the presence of an inoculant.

From the given bacteria (1.23), the bacterium (1.23a) *Bacillus pumilus* strain GB34 is used or employed in the present invention, in one embodiment in combination with compound (I-3), optionally in the presence of an inoculant.

From the given bacteria (1.26), the bacteria (1.26a) *Bacillus subtilis* strain GB03 and (1.26b) *Bacillus subtilis* var. *amyloliquefaciens* strain FZB24 are used or employed in the present invention in one embodiment in combination with compound (I-3), optionally in the presence of an inoculant.

From the given bacteria (1.27), the bacteria (1.27a) *Bacillus thuringiensis* subsp. *tenebrionis* NB 176, (1.27b) *Bacillus thuringiensis* subsp. *aizawaii* strain ABTS-1857, (1.27c) *Bacillus thuringiensis* subsp. *israelensis* strain AM 65-52 and (1.27d) *Bacillus thuriningiensis* subsp. *kurstaki* HD-1 are used or employed in the present invention in one embodiment in combination with compound (I-3), optionally in the presence of an inoculant.

According to the invention biological control agents that are summarized under the term "fungi" or "yeasts" are:

(2.1) *Ampelomyces quisqualis,* in particular strain AQ 10 (product known as AQ 10®), (2.2) *Aureobasidium pullulans,* in particular blastospores of strain DSM14940 or blastospores of strain DSM 14941 or mixtures thereof (product known as Blossom Protect®), (2.3) *Beauveria bassiana,* in particular strain ATCC 74040 (products known as Naturalis®), (2.4) *Candida oleophila,* in particular strain O (products known as Nexy®), (2.6) *Coniothyrium minions,* in particular strain CON/M/91-8 (products known as Contans®), (2.7) *Dilophosphora alopecuri* (products known as Twist Fungus®), (2.8) *Gliocladium catenulatum,* in particular strain J1446 (products known as Prestop®), (2.9) *Lecanicillium lecanii* (formerly known as *Verticillium lecanii*), in particular conidia of strain KV01 (products known as Mycotal®, Vertalec®), (2.10) *Metarhizium anisopliae,* in particular strain F52 (DSM 3884, ATCC No. 90448, products known as BIO 1020), (2.11) *Metschnikovia fructicola,* in particular the strain NRRL Y-30752 (products known as Shemer®), (2.12) *Microsphaeropsis ochracea* (products known as Microx®), (2.13) *Muscodor albus,* in particular strain QST 20799 (products known as QRD300), (2.14) *Nomuraea rileyi,* in particular strains SA86101, GU87401, SR86151, CG128 and VA9101, (2.15) *Paecilomyces lilacinus,* in particular spores of *P. lilacinus* strain 251 (AGAL 89/030550, products known as BioAct®, cf. Crop Protection 2008, 27, 352-361), or *Paecilomyces fumosoroseus,* (2.16) *Penicillium bilaii,* in particular strain ATCC22348 (products known as JumpStart®, PB-50, Provide), (2.17) *Pichia anomala,* in particular strain WRL-076, (2.18) *Pseudozyma flocculosa,* in particular strain PF-A22 UL (products known as Sporodex® L), (2.19) *Pythium oligandrum* DV74 (products known as Polyversum), (2.20) *Trichoderma asperellum,* in particular strain ICC 012 (products known as Bioten®), (2.21) *Trichoderma harzianum,* in particular *T. harzianum* T39 (products known as Trichodex®), and (2.22) *Beauveria brongniartii,* (2.23) *Trichoderma atroviride* strain CNCM No. I-1237 (products known as Esquive).

In one embodiment, from the given fungi and yeasts (2-1) to (2-23), the fungi and yeasts given under the numbers (2.10), (2.11), and (2.15) are to be used or employed in the present invention, in one embodiment in combination with compound (I-3), optionally in the presence of an inoculant.

It is preferred to use or employ in the present invention the compound of formula (I-3) in combination with (2.9) *Lecanicillium lecanii,* optionally in the presence of an inoculant.

It is preferred to use or employ in the present invention the compound of formula (I-3) in combination with (2.9a) *Lecanicillium lecanii* strain KV01, optionally in the presence of an inoculant.

It is preferred to use or employ in the present invention the compound of formula (I-3) in combination with (2.10) *Metarhizium anisopliae,* in particular strain F 52, optionally in the presence of an inoculant.

It is preferred to use or employ in the present invention the compound of formula (I-3) in combination with (2.11) *Metschnikovia fructicola,* in particular strain NRRL Y-30752, optionally in the presence of an inoculant.

It is preferred to use or employ in the present invention the compound of formula (I-3) in combination with (2.15) *Paecilomyces lilacinus,* in particular spores of *P. lilacinus* strain 251, optionally in the presence of an inoculant.

It is preferred to use or employ in the present invention the compound of formula (I-3) in combination with (2.14) *Nomuraea rileyi,* optionally in the presence of an inoculant.

According to the invention biological control agents that are summarized under the term "protozoas" are:

(3.1) *Nosema locustae,* and (3.2) *Vairimorpha.*

It is preferred to use or employ in the present invention the compound of formula (I-3) in combination with (3.1) *Nosema locustae,* optionally in the presence of an inoculant.

It is preferred to use or employ in the present invention the compound of formula (I-3) in combination with (3.2) *Vairimorpha,* optionally in the presence of an inoculant.

According to the invention biological control agents that are summarized under the term "viruses" are:
- (4.1) Gypsy moth (*Lymantria dispar*) nuclear polyhedrosis virus (NPV), (4.2) Tussock moth (*Lymantriidae*) NPV, (4.3) *Heliothis* NPV, (4.4) Pine sawfly (*Neodiprion*) NPV, and (4.5) Codling moth (*Cydia pomonella*) granulosis virus (GpGV).

It is preferred to use or employ in the present invention the compound of formula (I-3) in combination with (4.1) Gypsy moth nuclear polyhedrosis virus (NPV), optionally in the presence of an inoculant.

It is preferred to use or employ in the present invention the compound of formula (I-3) in combination with (4.2) Tussock moth NPV, optionally in the presence of an inoculant.

It is preferred to use or employ in the present invention the compound of formula (I-3) in combination with (4.3) *Heliothis* NPV, optionally in the presence of an inoculant.

It is preferred to use or employ in the present invention the compound of formula (I-3) in combination with (4.4) Pine sawfly NPV, optionally in the presence of an inoculant.

It is preferred to use or employ in the present invention the compound of formula (I-3) in combination with (4.5) Codling moth granulosis virus (GpGV), optionally in the presence of an inoculant.

According to the invention biological control agents that are summarized under the term "entomopathogenic nematode" are:
- (5.1) *Steinernema scapterisci*, (5.2) *Steinernema feltiae*, (5.3) *Steinernema carpocapsae*, (5.4) *Heterorhabditis heliothidis*, and (5.5) *Xenorhabdus luminescence*.

It is preferred to use or employ in the present invention the compound of formula (I-3) in combination with (5.1) *Steinernema scapterisci*, optionally in the presence of an inoculant.

It is preferred to use or employ in the present invention the compound of formula (I-3) in combination with (5.2) *Steinernema feltiae*, optionally in the presence of an inoculant.

It is preferred to use or employ in the present invention the compound of formula (I-3) in combination with (5.3) *Steinernema carpocapsae*, optionally in the presence of an inoculant.

It is preferred to use or employ in the present invention the compound of formula (I-3) in combination with (5.4) *Heterorhabditis heliothidis*, optionally in the presence of an inoculant.

It is preferred to use or employ in the present invention the compound of formula (I-3) in combination with (5.5) *Xenorhabdus luminescence*, optionally in the presence of an inoculant.

Examples for inoculants which may be used or employed according to the invention are bacteria of the genus *Rhizobium leguminosarum, Rhizobium tropici, Rhizobium loti, Rhizobium trifolii, Rhizobium meliloti, Rhizobium fredii, Azorhizobium caulinodans, Pseudomonas, Azospirillum, Azotobacter, Streptomyces, Burkholdia, Agrobacterium, Endo-, Ecto-, Vesicular-Arbuscular* (VA) *Mycorhizza*. It is preferred to use soil-inoculants.

The amount of the biological control agent selected from bacteria, in particular spore-forming bacteria, fungi or yeasts, protozoas, viruses, and entomopathogenic which is used or employed in combination with a compound (I-1), (I-2) or (I-3), preferably with a compound (I-3), optionally in the presence of an inoculant, depends on the final formulation as well as size or type of the plant, plant parts, seeds, harvested fruits and vegetables to be treated. Usually, the biological control agent to be employed or used according to the invention is present in about 0.0001% to about 80% (w/w), preferably in about 5% to about 75% (w/w), more preferably about 10% to about 70% (w/w) of its solo-formulation or combined-formulation with the compound (I-1), (I-2) or (I-3), and optionally the inoculant.

If bacteria, fungi or yeasts are selected as biological control agent, in particular those who are named as being preferred, namely (2.10), (2.11), and (2.15), it is preferred that these biological control agents or, e.g., their spores are present in a solo-formulation or the combined-formulation in a concentration of at least $10^5$ colony forming units (e.g. spores per gram, yeast cells per gram) such as $10^5$-$10^{12}$ cfu/g, preferably $10^6$-$10^{11}$ cfu/g, more preferably $10^7$-$10^{10}$ cfu chu/g and most preferably $10^9$-$10^{10}$ cfu/g at the time point of applying biological control agents on a plant or plant parts such as seeds, fruits or vegetables. Also references to the concentration of biological control agents in form of, e.g., spores or cells—when discussing ratios between the amount of a compound (IA) and the amount of a preparation of a biological control agent—are made in view of the time point when a biological control agent is applied on a plant or plant parts such as seeds, fruits or vegetables.

Also the amount of compound (I-1), (I-2) or (I-3) which is used or employed in combination with the biological control agent selected from bacteria, in particular spore-forming bacteria, fungi or yeasts, protozoas, viruses, and entomopathogenic nematodes, optionally in the presence of an inoculant, depends on the final formulation as well as size or type of the plant, plant parts, seeds, harvested fruit or vegetable to be treated. Usually, the compound (I-1), (I-2) or (I-3) to be employed or used according to the invention is present in about 0.1% to about 80% (w/w), preferably 1% to about 60% (w/w), more preferably about 10% to about 50% (w/w) of its solo-formulation or combined-formulation with the biological control agent selected from bacteria, in particular spore-forming bacteria, fungi or yeasts, protozoas, viruses, and entomopathogenic nematodes, and optionally the inoculant.

It is preferred to employ or use the compound (I-1), (I-2) or (I-3) and the biological control agent selected from bacteria, in particular spore-forming bacteria, fungi or yeasts, protozoas, viruses, and entomopathogenic nematodes, and if present also the inoculant in an synergistic weight ratio. The skilled person understands that these ratios refer to the ratio within a combined-formulation as well as to the calculative ratio of compound (I-1), (I-2) or (I-3) and the biological control agent described herein when both components are applied as mono-formulations to a plant to be treated.

The ratio can be calculated based on the amount of a compound of formula (I), preferably compound (I-1), (I-2) or (I-3), at the time point of applying said component of a combination according to the invention to a plant or plant part and the amount of a biological control agent shortly prior (e.g., 48 h, 24 h, 12 h, 6 h, 2 h, 1 h) or at the time point of applying said component of a combination according to the invention to a plant or plant part.

The application of a compound (I-1), (I-2) or (I-3) and a biological control agent to a plant or a plant part can take place simultaneously or at different times as long as both components are present on or in the plant after the application(s). In cases where the biological control agent and a compound of formula (I), preferably compound (I-1), (I-2) or (I-3), are applied at different times and a compound of formula (I) is applied noticeable prior to a biological control agent (e.g. 14, 10, 7, 5, 3, 1 day prior to application of a biological control agent), the skilled person can determine the concentration of a compound of formula (I), preferably compound (I-1), (I-2) or (I-3), on/in a plant by chemical analysis known in the art, at the time point or shortly before the time point of applying a biological control agent. Vice versa, when a biological control agent is applied to a plant first, the concentration of a biological control agent can be determined using tests as described herein that are also known in the art, at the time point or shortly before the time point of applying a compound of formula (I), preferably compound (I-1), (I-2) or (I-3).

In particular, the synergistic weight ratio of a compound (I-1), (I-2) or (I-3) to a bacteria/bacteria spore preparation, in particular a preparation of spore forming bacteria, is in the range of 500:1 to 1:1000, preferably in the range of 500:1 to 1:500, more preferably in a range of 500:1 to 1:300. It has to be noted that these ratio ranges refer to a bacteria/bacteria spores preparation (to be combined with a compound (I-1), (I-2) or (I-3) or a preparation of a compound (I-1), (I-2) or (I-3)) of around $10^{10}$ bacteria/spores per gram preparation of said bacteria/bacteria spores. For example, a ratio of 1:100 means 1 weight part of a compound (I-1), (I-2) or (I-3) and 100 weight parts of a bacteria/bacteria spore preparation having a bacteria/bacteria spore concentration of $10^{10}$ bacteria/bacteria spores per gram bacteria/bacteria spore preparation are combined (either as a solo formulation, a combined formulation or by separate applications to plants so that the combination is formed on the plant).

The bacteria/bacteria spore concentration of preparations can be determined by applying methods known in the art and described in this application. To compare weight ratios of a compound (I-1), (I-2) or (I-3) to a bacteria/bacteria spore preparation, the skilled person can easily determine the factor between a preparation having a bacteria/bacteria spore concentration different from $10^{10}$ bacteria/bacteria spores per gram bacteria/bacteria spore preparation and a preparation having a bacteria/bacteria spore concentration of $10^{10}$ bacteria/bacteria spores per gram preparation to calculate whether a ration of a compound (I-1), (I-2) or (I-3) to a bacteria/bacteria spore preparation is within the scope of the above listed ratio ranges.

In one preferred embodiment, when a biological control agent is *Bacillus subtilis*, preferably strain GB 03, the synergistic weight ratio of a compound (I-1), (I-2) or (I-3), preferably compound I-3, to a preparation of *B. subtilis* of $10^{10}$ *B. subtilis* spores per grain preparation is between 10:1 and 1:50 or even between 1:1 and 1:20 such as between 1:1 and 1:15 or between 1:3 and 1:10.

In one preferred embodiment, when a biological control agent is *Bacillus thuringiensis*, preferably strain ABTS-1857, the synergistic weight ratio of a compound (I-1), (I-2) or (I-3), preferably compound I-3, to a preparation of *B. thuringiensis* of $10^{10}$ *B. thuringiensis* spores per gram preparation is between 500:1 and 1:100 or even between 500:1 and 1:50 such as between 450:1 and 1:25 or between 400:1 and 1:15.

In one preferred embodiment, when a biological control agent is *Bacillus amyloliquefaciens*, preferably strain FZB 42, the synergistic weight ratio of a compound (I-1), (I-2) or (I-3), preferably compound I-3, to a preparation of *B. amyloliquefaciens* of $10^{10}$ *B. amyloliquefaciens* spores per gram preparation is between 100:1 and 1:100 or even between 10:1 and 1:100 such as between 1:1 and 1:25, between 1:1 and 1:10 or between 1:1.25 and 1:5.

In particular, the synergistic weight ratio of a compound (I-1), (I-2) or (I-3) to a fungi or yeast preparation is in the range of 100:1 to 1:20.000, preferably in the range of 50:1 to 1:10.000 or even in the range of 50:1 to 1:1000. It has to be noted that before mentioned ratios ranges refer to spore/cell preparations of fungi or yeast of around $10^{10}$ spores (fungi) or cells (yeast) per gram preparation of said fungi or yeast. For example, a ratio of 1:100 means 1 weight part of a compound (I-1), (I-2) or (I-3) and 100 weight parts of a spore preparation of a fungi or yeast having a spore/cell concentration of $10^{10}$ spores/cells per gram preparation of said fungi or yeast (without compound (I-1), (I-2) or (I-3) or a preparation of compound (I-1), (I-2) or (I-3)).

The spore/cell concentration of preparations can be determined by applying methods known in the art and described in this application. To compare weight ratios of a compound (I-1), (I-2) or (I-3) to a fungi or yeast preparation, the skilled person can easily determine the factor between a preparation having a spore/cell concentration different from $10^{10}$ spores/cells per gram fungi/yeast preparation and a preparation having a spore/cell concentration of $10^{10}$ spores/cells per gram preparation to calculate whether a ration of a compound (I-1), (I-2) or (I-3) to a fungi or yeast preparation is within the scope of the above listed ratio ranges.

In one preferred embodiment, when a biological control agent is *Metschnikowia fructicola*, preferably strain NRRL Y-30752, the synergistic weight ratio of a compound (I-1), (I-2) or (I-3), preferably compound I-3, to a preparation of *M. fructicola* of $10^{10}$ *M. fructicola* cells per grain preparation is between 10:1 and 1:100 or even between 1:1 and 1:25 such as between 1:5 and 1:25 or between 1:10 and 1:20.

In another preferred embodiment, when a biological control agent is *Paecilomyces lilacinus*, preferably strain 251, the synergistic weight ratio of a compound (I-1), (I-2) or (I-3), preferably compound I-3, to a preparation of *P. lilacinus* of $10^{10}$ *P. lilacinus* spores per gram preparation is between 500:1 and 1:500 or even between 1:1 and 1:500 such as between 1:200 and 1:300 or between 1:200 and 1:250.

In another preferred embodiment, when a biological control agent is *Metarhizium anisopliae*, preferably strain F52, the synergistic weight ratio of a compound (I-1), (I-2) or (I-3), preferably compound I-3, to a preparation of *M. anisopliae* of $10^{10}$ *M. anisopliae* spores per gram preparation is between 100:1 and 1:100 or even between 10:1 and 1:20 such as between 1:1 and 1:10 or between 1.1:1 and 1.1:3.75.

In one embodiment of the present invention, a biological control agent is a fungus or yeast and the amount of a fungus spore or yeast cells preparation of $10^{10}$ spores/cells which is dispersed/ha is at least 50 g/ha, such as 50-7500 g/ha, 50-5000 g/ha, 50-2500 g/ha, at least 250 g/ha (hectare), at least 500 g/ha or at least 1000 g/ha. The skilled person can easily calculate the amount of preparation/ha having a fungus spore preparation different from $10^{10}$ spores to match this criterion.

In one embodiment of the present invention, a biological control agent is *Paecilomyces lilacinus*, e.g., strain 251, and the amount of a fungus spore preparation (based on a fungus spore preparation of $10^{10}$ spores/g preparation) which is dispersed/ha is at least 50 g/ha; at least 100 g/ha; at least 1000 g/ha; at least 2500 g/ha, such as 2500-7500 g/ha, 2500-6000 g/ha; or at least 4000 g/ha, such as 4000-6000 g/ha, e.g. around 5000 g/ha.

In one embodiment of the present invention, a biological control agent is *Metarhizium anisopliae*, e.g., strain F52, and the amount of a fungus spore preparation (based on a fungus spore preparation of $10^{10}$ spores/g preparation) which is dispersed/ha is at least 50 g/ha, such as 50-7500 g/ha, 50-1000 g/ha, 50-250 g/ha such as 90-250 g/ha, or 90-225 g/ha.

In one embodiment of the present invention, a biological control agent is *Metschnikowia fructicola*, and the amount of a yeast cell preparation (based on a yeast spore preparation of $10^{10}$ spores/g preparation) which is dispersed/ha is at least 50 g/ha, such as 50-5000 g/ha, 50-2000 g/ha; at least 500 g/ha; at least 1000 g/ha, such as 1000-2000 g/ha.

In one embodiment of the present invention, a biological control agent is a bacterium and the amount of a fungus spore or yeast cells preparation of $10^{10}$ spores/cells which is dispersed/ha is at least 0.1 g/ha. The skilled person can easily calculate the amount of preparation/ha having a bacteria/bacteria spore preparation different from $10^{10}$ spores to match this criterion.

In one embodiment of the present invention, a biological control agent is *B. thuringiensis* and the amount of the spore preparation (based on a spore preparation of $10^{10}$ spores/g preparation) which is dispersed/ha is at least 0.1 g/ha (hectare), such as 0.1-5000 g/ha, 0.1-10 g/ha, 0.1-2 g/ha; at least 0.15 g/ha, such as 0.15-1 g/ha, 0.15-0.9 g/ha, or even 0.15-0.81 g/ha.

In another embodiment of the present invention, a biological control agent is *B. subtilis*, e.g., strain GB 03, and the amount of the spore preparation (based on a spore preparation of $10^{10}$ spores/g preparation) which is dispersed/ha is at least 50 g/ha such as 50-5000 g/ha, 50-2500 g/ha, 50-500 g/ha; at least 100 g/ha, or at least 250 g/ha, such as 100-500 g/ha or 250-350 g/ha, e.g., around 300 g/ha.

In another embodiment of the present invention, a biological control agent is *B. amyloliquefaciens* and the amount of the spore preparation (based on a spore preparation of $10^{10}$ spores/g preparation) which is dispersed/ha is at least 500 g/ha, such as 500-8000 g/ha, 2500-7500 g/ha, or 4000 g/ha to 6000 g/ha such as around 5000 g/ha.

In yet another embodiment of the invention, a biological control agent is a bacterium, fungus or yeast and the amount of a bacteria/bacteria spore, fungus spore or yeast cell preparation of $10^{10}$ spores/cells which is mixed with seeds (e.g., in seed treatment) is at least 0.1 g/kg seeds such as 0.1 g/kg-10 g/kg, 0.1 g/kg 1 g/kg. The skilled person can easily calculate the amount of preparation/ha having a bacteria/bacteria spore, fungus spore or yeast cell preparation different from $10^{10}$ spores/g preparation to match this criterion.

In one embodiment of the present invention, a biological control agent is a virus and the concentration of the virus after dispersal is at least 50 g/ha such as 50-7500 g/ha, 50-2500 g/ha, 50-1500 g/ha; at least 100 g/ha or at least 150 g/ha.

In one embodiment of the present invention, a biological control agent is a virus, such as *Cydia pomonella* granulosis virus and the concentration of the virus after dispersal is at least 50 g/ha (hectare) such as 50-5000 g/ha, 50-2500 g/ha or 50-1500 g/ha. In a preferred embodiment, the concentration is around 1000 gala such as 900-1100 g/ha. However, also other concentrations are suitable such as such as 100 1500 g/ha or 100 250 g/ha.

In one embodiment of the present invention, a biological control agent is a nematode and the concentration of the nematodes is at least $10^6$ nematodes/ha, e.g., larval stage nematodes/ha, such as $10^6$-$10^{1'}$ nematodes/ha, e.g., larval stage nematodes/ha, $10^6$-$10^{12}$ nematodes/ha, e.g., larval stage nematodes/ha, at least $10^8$ nematodes/ha, e.g., larval stage nematodes/ha such as $10^8$-$10^{15}$ nematodes/ha, e.g., larval stage nematodes/ha, $10^8$-$10^{12}$ nematodes/ha, e.g., larval stage nematodes/ha; or at least $10^9$ nematodes/ha, e.g., larval stage nematodes/ha, such as $10^9$ $10^{15}$ nematodes/ha, e.g., larval stage nematodes/ha or $10^9$-$10^{12}$ nematodes/ha, e.g., larval stage nematodes/ha.

In one embodiment of the present invention, the ratios between bacteria (such as *Bacillus amyloliquefaciens, Bacillus subtilis, Bacillus thuringiensis* subsp. *aizawai, Bacillus thuringiensis* subsp. *israeliensis, Bacillus thuringiensis* subsp. *kurstaki, Bacillus thuringiensis* subsp. *tenebrionis, Bacillus pumilus, Bacillus cereus*) and compound (1-1), (1-2) or (1-3) in a solo- or combined-formulation or on or in a plant to be treated or its surrounding, habitat or storage space is between 500:1 to 1:500, such as between 250:1 to 1:250 or even 25:1 to 1:25.

In one embodiment of the present invention, the ratios between fungi (such as *Metarhizium anisopliae, Paecilomyces lilacinus, Beauveria bassiana, Nomuraea rileyi*) and compound (1-1), (1-2) or (1-3) in a solo- or combined-formulation or on or in a plant to be treated or its surrounding, habitat or storage space is between 125:1 to 1:1250 or even 25:1 to 1:250.

In one embodiment of the present invention, the ratios between nematodes (such as *Steinernema feltiae* and *Steinernema carpocapsae*) and compound (1-1), (1-2) or (1-3) in a solo- or combined-formulation or on or in a plant to be treated or its surrounding, habitat or storage space is between 125:1 to 1:125, between 100:1 to 1:25 or even 50:1 to 1:5.

The application rate of the biological control agent selected from bacteria, in particular spore-forming bacteria, fungi or yeasts, protozoas, viruses, and entomopathogenic nematodes to be employed or used according to the present invention may vary. The skilled person is able to find the appropriate application rate by way of routine experiments.

Moreover, the skilled person is aware how to store biological control agents which are part of the present invention. In general, biological control agents which are part of the present invention are kept/stored at temperatures below 40° C., for example at temperatures below 37° C. such as between 4° C. and 35° C. or between 4° C. and 27° C.

The skilled person is aware under which conditions biological control agents which are part of the present invention should be applied to a plant or parts thereof. In general, biological control agents are part of the present invention are applied to a plant or parts thereof at temperatures below 40° C., for example at temperatures between 15° C. and 32° C. or 20° C. and 27° C.

Microorganisms such as fungi or bacteria can be obtained by conventional fermentation processes. The fermentation can be carried out using solid, semi-solid or liquid nutrient media. If spores such as conidia are used, preference is given to solid or semi-solid nutrient media. The nutrient media contain the nutrients suitable and known for the cultivation of the respective microorganisms, in particular one or more metabolizable carbon sources or nitrogen sources and mineral salts. The fermentation is generally carried out at temperatures between about 3° C. and about 40° C., preferably between 20° C. and 35° C. For example, a representative fermentation is described in U.S. Pat. No. 5,804,208.

A fermentation process comprises in general the steps of a) incubating spores such as conidia of a microorganism in or on a nutrition medium (such as agar with further additives such as oatmeal); b) separating spores such as conidia from the nutrition medium after the incubation time, (e.g., by shake off the conidia from the medium, centrifuging, filtrating); and optionally c) preparing an emulsion of said isolated conidia.

The skilled person is well aware how to adapt fermentation to a given microorganism such as fungi or bacteria. In the following, several fermentations are exemplified in more detail. These examples are not meant to limit the scope of the present invention.

Fungi

The fungus *Metarhizium anisopliae*, strain DSM 3884, is known from EP 0 268 177. The production of conidia of *Metarhizium anisopliae* is exemplified in EP 0 794 704 (U.S. Pat. No. 5,804,208).

A nutrition medium such as oatmeal agar (e.g., composition: 30 g of oat flakes and 20 g of agar) in a Petri dish was inoculated with, e.g., 3 week old conidia of the *Metarhizium anisopliae* strain DSM 3884. The incubation time to multiply the conidia is, e.g., 3, 4, 5, or 6 days. The incubation temperature can be around 7° C. to around 40° C., e.g. 22° to 25° C.

The formed conidia was isolated by, e.g. shaking off the conidia. The conidia can be stirred with 50 ml of water containing 1% of a non-ionic emulsifier such as an emulsifier based on polyoxy-ethylene (20) sorbitan monolaurate (Tween 20®) until a suspension was obtained in which the conidia was present as isolated particles. The conidia titer was and can be determined using, e.g., a Neubauer chamber. The conidia can be stored in closed cases under dry conditions, preferably at temperatures between 0° and 25° C.

*Paecilomyces lilacinus* strain 251 was isolated from infected nematode eggs in the Philippines, and correctly described taxonomically in 1974. Optimal laboratory growth of *Paecilomyces lilacinus* strain 251 occurs at 21-27° C., and does not grow or survive above 36° C. (U.S. Environmental Protection Agency, *P. lilacinus* strain 251 Fact sheet). The following cultivation of *Paecilomyces lilacinus* is exemplified in Patent Application WO/1994/025579:

*Paecilomyces lilacinus* (Thorn) Samson (CBS 143.75), obtained e.g. from the CBS (Central Bureau of Fungal Cultures) in Baarn (The Netherlands), can be maintained on Potato Dextrose Agar (PDA; Difco laboratories) at 25° C. A conidial suspension was obtained by adding sterilized water (e.g., 5 ml) to a Petri dish containing sporulating mycelium and scraping the surface with a glass rod. Liquid cultures were obtained by inoculating conidia of the fungus to minimal salt medium or corn flour medium supplemented with the substrate. The minimal salt medium (MM) consists of 4.56 g H2PO4, 2.77 g KH2 HP04, 0.5 g MgS04. 7H20 and 0.5 g KCI/1, pH 6.0. Mycelium can be obtained by centrifuging a, e.g., 6 day old culture of conidia of *Paecilomyces lilacinus*. For example, cultures can be grown in a shaking water bath for several days at 30° C. and 125 strokes per minute, Culture filtrates were obtained by centrifuging cultures for, e.g., 45 min at 9000 g.

The preparation of *Metschnikowia fructicola* is exemplified in U.S. Pat. No. 6,994,849:

The yeast species *Metschnikowia fructicola* was isolated from the surface of grape bevies (cv. Superior) grown in the central part of Israel. At various stages, individual berries were submersed in sterile distilled water in 100 ml beakers and shaken vigorously for 2 hours on rotary shaker at 120 rpm. Aliquots of 100 ml were removed from the wash liquid and plated on PDA (Potato Dextrose Agar; DIFCO Laboratories, U.S.A.) medium. Following 4-5 days of incubation, yeast colonies were picked randomly according to colony characteristics (color and morphology) and streaked individually on fresh medium to obtain biologically pure cultures. Cultures were further purified by repeated streaking on PDA. Identification and characterization of the new species was done at the Microbial Genomics and Bioprocessing center, USDA-ARS, Peoria, Ill., USA. *Metschnikowia fructicola* was deposited at the NRRL under the number Y-30752. This deposit has been made in compliance with the terms of the Budapest Treaty.

*Metschnikowia fructicola* was propagated under aerobic conditions at temperatures ranging from 5° C. to 37° C. Optimal growth temperature is between 20° C. and 27° C. The yeast grows in liquid medium (nutrient broth; Droby et al., 1989) with a neutral pII. The cell density of the yeast generally reached its maximum (stationary stage) growth in 24-48 hours. For laboratory and small scale tests growth in Erlenmeyer flasks containing the medium and shaken on a rotary shaker was suitable. For large scale and commercial tests, fermentation tanks and industrial growth media were preferred. The yeast cells were harvested by centrifugation using conventional laboratory or industrial centrifuges.

Bacteria

*Bacillus thuringiensis* were cultured using media and fermentation techniques known in the art (see, for example, Rogoff et al., 1969, J. Invertebrate Path. 14: 122-129; Dulmage et al., 1971, J. Invertebrate Path. 18: 353-358; Dulmage et al., in Microbial Control of Pests and Plain Diseases, H. D. Burges, ed., Academic Press, N.Y., 1980). Upon completion of the fermentation cycle, the supernatant can be recovered by separating *Bacillus thuringiensis* spores and crystals from the fermentation broth by means well known in the art, e.g., centrifugation ultrafiltration, evaporation, and/or spray-drying (see also WO 1996001563 which is herewith incorporated by reference in its entirety).

The following culturing of *Bacillus thuringiensis* is e.g. exemplified in U.S. Pat. No. 5,508,032:

A subculture of *Bacillus thuringiensis* isolates can be used to inoculate the following medium, a peptone, glucose, salts medium: Bacto Peptone 7.5 g/l Glucose, 1.0 g/l $KH_2PO_4$, 3.4 g/l $K_2HPO_4$, 4.35 g/l salt solution, 5.0 ml/l $CaCl_2$ solution, 5.0 ml/l salts solution (100 ml) $MgSO_4$-$7H_2O$, 2.46 g $MnSO_4$—$H_2O$, 0.04 g $ZnSO_4$-$7H_2O$, 0.28 g $FeSO_4$-$7H_2O$, 0.40 g $CaCl_2$ solution (100 ml), $CaCl_2 2H_2O$, 3.66 g pH 7.2.

The salts solution and $CaCl_2$ solution were sterilized (e.g., filter-sterilized) and added to the sterilized (e.g., autoclaved and cooked) broth at the time of inoculation. Flasks were incubated at around 30° C. on a rotary shaker at 200 rpm for 64 hours. The procedure can be readily scaled up to large feinientors by procedures well known in the art. The *Bacillus thuringiensis* spores and crystals, obtained in the fermentation, can be isolated by procedures well known in the art. A frequently-used procedure is to subject the harvested fermentation broth to separation techniques, e.g., centrifugation.

The bacteria *Bacillus subtilis* is a naturally occurring bacteria found in soils all over the world. *Bacillus subtilis* strain QST713 was isolated in 1995 by AgraQuest Inc. from soil in a California peach orchard. This product is applied to foliage (NYDEC 2001). In contrast, *Bacillus subtilis* strain GB03 (Kodiak®) was discovered in Australia in the 1930's and is applied either as a seed treatment or directly to soil. Neither strain is considered a genetically modified organism (Cornell University: Organic Resource Guide, Material fact sheet—*Bacillus subtilis*)

Isolation of *Bacillus subtilis* and related strains from soil: To isolate wild *Bacillus subtilis* strains, e.g., 2 g soil samples were dissolved in 2 ml of 10 mM Tris/HCl (pH 7.2) and then boiled at 95° C. for 5 min. From these samples, 0.1 ml of each sample was then spread onto LB plates and incubated at 37° C.

Sporulation assay: *Bacillus subtilis* strains were grown in 26 SG medium at 37° C. and sporulation was assayed at 24 hours after the end of the exponential phase. The number of spores per ml culture was determined by identifying the number of heat-resistant colony forming units (80° C. for 10 min) on LB plates.

*Bacillus subtilis*, strain Marburg, was grown aerobically in heart infusion broth (Difco Laboratories, Detroit, Mich.) on shaker at about 37° C. From an overnight culture 4 drops were inoculated into 70 ml of pre warmed broth. Growth was measured as optical density at 620 nm. Cells were collected after 3.5-4.5 hours in the exponential phase of growth. Centrifugation was carried out at room temperature for 15 min at 7000 g (Nanninga, The Journal of Cell Biology. Volume 48, 1971•pages 219-224).

*Bacillus subtilis* is active in temperatures between 7° C. and 45° C.

*Bacillus amyloliquefaciens* strain FZB42, was originally isolated from infested soil in Germany (Krebs et al. (1998) J Plant Dia Prot 105: 181-197, Chen et al. (2007), Nature Biotechnol. 25(9):1007-14.). *Bacillus amyloliquefaciens* strain FZB42 was cultivated in Luria broth (LB—1% w/v peptone, 0.5% w/v yeast extract, 0.5% w/v NaCl) at 30° C. (Fan et al. (2011), Journal of Biotechnology 151: 303-311). The bacteria were grown in Landy medium as described in Koumoutsi et al. (2004), J. Bacteriol. 186: 1084 1096. To prepare surface cultures, the strains were grown in petri dishes containing 1.5% Landy agar for 24 h at 37° C. and stored at room temperature prior to MALDI-TOF-MS analysis. Fermentation in liquid media was carried out in flasks at 30° C. and 180 rpm in a shaker.

Viruses

*Cydia pomonella* granulosis viruses (CpGV) which are used in the products MADEX (Andermatt Biocontrol) and Granupom (Probis GmbH) are deposited since 2005 at the German Collection of Microorganisms and Cell Cultures (DSMZ). Isolates used for the production of MADEX (Andermatt Biocontrol), Granupom (Probis GmbH), VIRGO (SipcamS.p.A.) and CARPOVIRUSINE (Arysta LifeScience S.A.S) were all derived from the Mexican isolate originally isolated in 1963 and are not genetically modified. (Virus accession number: GV-000))

The identity of the virus produce can be bioanalytically checked against the parent strain by SDS-polyacrylamide-gel electrophoresis of the virus protein sand by Restriction endonuclease analysis of viral DNA.

Prior to DNA isolation the test item has to be purified. The purified CpCIV OB pellet is resuspended in 1 ml sterile water and the CpGV OB concentration is enumerated in the Petroff-Hausser counting chamber. The concentration of active *Cydia pomonella* Granulosis virus (CpGV) is determined by means of a quantitative bioassay. The granules (occlusion bodies) of CpGV are counted under the light microscope. The virus titer in the end-use product is adjusted to the requested granules/I (Assessment Report: *Cydia pomonella* Granulovirus (CpGV)—Mexican Isolate (2007).

CpGV derives from the Mexican isolate of CpGV (Tanada, (1964), J. Insect Pathol. 6: 378-380) and is propagated in larvae of *Cydia pomonella*. Infected larvae are homogenized and centrifuged in 50% sucrose (w/w). The pellet is resuspended and the granules are purified by, e.g., centrifugation through a linear 50% to 60% (w/w) sucrose gradient, generating a virus band which is then repeatedly washed in Tris buffer and pelleted to remove residual sucrose. (Jehle et al., (1992), Journal of general virology, 73: 1621-1626).

Entomopathogenic Nematodes

Nematodes can be reared in liquid culture techniques (see, e.g., U.S. Pat. No. 5,023,183 which is herewith incorporated by reference in its entirety) and stored, for example, as eggs, larvae in suspension cultures or in clay powder or adult nematodes, e.g. in clay powder. Nematodes can be held in the refrigerator (2-6° C.) until use for up to 4 weeks and can be reactivated by suspension in warm water (>12° C.).

One method to isolate entomopathogenic nematodes from soil is described by Cairns, 1960, Folia parasitica 47: 315-318. For soil samples, a sieving-decanting method was employed with final isolation of the nematodes from the sieving debris using a Baermann funnel with cotton filter. For this method, which is commonly applied for the extraction of plant-parasitic and soil nematodes (Southey (1986), Ministry of Agriculture, Fisheries and Food Reference Book No. 402, 202 pp. HMSO, London, UK), 250 ml soil was used. The nematode suspension was fixed, checked for the presence of entomopathogenic nematodes using an inverted light microscope, and the number of Steinernema specimens was determined. Species identification was mostly done at high microscopical magnification using morphological characters of the infective-stage juveniles.

Entomopathogenic nematodes can be mass-produced by in-vivo or in-vitro methods. Larvae of *Galleria mellonella* are most commonly used to rear nematodes because of their commercial availability. Several researchers (e.g., Dutky et al. (1964), J. Insect Pathol. 6: 417-422, or Flanders et al. (1996), J. Econ. Entomol. 89: 373-380) have described the methods of nematode infection, inoculation, and harvesting. Using the in-vivo process, yields between $0.5 \times 10^5$-$4 \times 10^5$ infective juveniles, depending on the nematode species, have been obtained. During the past few years a distinct cottage industry has emerged in the USA which utilizes the in-vivo process for nematode mass-production for sale, especially in the home lawn and garden markets. The in-vivo process, however, lacks any economy of scale; the labor, equipment, and material (insect) costs increase as a linear function of production capacity. Perhaps even more important is the lack of improved quality while increasing scale. The in-vivo nematode production is increasingly sensitive to biological variations and catastrophes as scale increases. Several formulations have been developed for the storage and application of entomopathogenic nematodes. The shelf life of different nematode-based products varies depending on the formulation, nematode species and temperature. In the simplest type of formulation, the nematodes are impregnated onto moist carrier substrates providing substantial interstitial spaces leading to increased gas exchange. Such carriers include polyether polyurethane sponge, cedar shavings, peat, vermiculite, etc. Nematodes held on the sponge need to be handsqueezed into water before application, whereas from the other carriers they may be applied directly to the soil as mulch (Neves et al., Neotropical Entomology, vol. 30, no. 2, Londrina, June 2001, ISSN 1519-566X).

A bioassay to determine nematode viability is described, e.g., in Simser ((1992) J. of Nematology 24(31:374-378). The Nematode viability was verified by host bioassay. Late instar larvae of the greater wax moth, *Galleria mellone*, were buried 2.5 on deep between plants before nematode application (four larvae per replicate), collected after 7 days, placed in petri dishes (9 cm diameter) and held in darkness at ca. 25° C. Insect mortality (>90%) and subsequent nematode propagation with cadavers demonstrated infectivity of the nematodes. The skilled person is well aware how to adopt this kind of bioassay to different nematode species.

The preferred application rate of bacteria as biological control agent, in particular of spores of the bacteria (1.26a), namely *B. subtilis* strain GBO3, lies in the range of 0.1 to 3 kg/ha.

The preferred application rate of fungi as biological control agent, in particular the fungi *Metarhizium anisopliae* strain F 52 lies in the range of 0.1 to 3 kg/ha The preferred application rate of yeasts as biological control agent, in particular the yeast *Metschnikowia fructicola* strain NRRL Y-30752 lies in the range of 0.05 to 8 kg/ha.

The preferred application rate of protozoa, viruses, and entomopathogenic nematodes as biological control agents lies in the range of 0.5 to 10 kg/ha.

It is generally preferred to use or employ the compound (I-1), (I-2) or (I-3) and the biological control agent selected from bacteria, in particular spore-forming bacteria, fungi or yeasts, prolozoas, viruses, and entomopathogenic nematodes, and if applicable also the inoculant on horticultural crops, such as cotton, flax, grapevines, fruit, vegetable, such as *Rosaceae* sp. (for example pomaceous fruit, such as apples and pears, but also stone fruit, such as apricots, cherries, almonds and peaches and soft fruit such as strawberries), *Ribesioidae* sp., *Juglandaceae* sp., *Betulaceae* sp., *Anacardiaceae* sp., *Fagaceoe* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit), *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leek, onions), *Papilionaceae* sp. (for example peas); major crop plants, such *Gramineae* sp. (for example maize, lawn, cereals such as wheat, rye, rice, barley, oats, millet and triticale), *Poaceae* sp. (for example sugarcane), *Asteraceae* sp. (for example sunflowers), *Brassicaceae* sp. (for example white cabbage, red cabbage, broccoli, cauliflowers, Brussels sprouts, pak choi, turnip cabbage, garden radish, and also oilseed rape, mustard, horseradish and cress), *Fabacae* sp. (for example beans, peas, peanuts), *Papilionaceae* sp. (for example soya beans), *Solanaceae* sp. (for example potatoes), *Chenopodiaceae* sp. (for example sugar beet, fodder beet, Swiss chard, beetroot); crop plants and ornamental plants in garden and forest; and also in each case genetically modified varieties of these plants.

Horticultural crops particularly includes carrots, pumpkin, squash, zucchini, potato, sweet corn, onions, ornamentals, medicinal herbs, culinary herbs, tomatoes, spinach, pepper, melon, lettuce, cucumber, celery, beets, cabbage, cauliflower, broccoli, Brussels sprouts, turnip cabbage, kale, radish, rutabaga, turnip, asparagus, bean, pea, apples, raspberry, strawberry, banana, mango, grapes, peaches, pears, guava, pineapple, pomegranate, garlic, *capsicum*, chili, radish, star fruit, tapioca, walnuts, lemon, mandarin, mangold, mushroom, olive, orange, papaya, paprika, passion fruit, peanuts, pecan nuts, prune, pistachio nuts, persimmon, pamplemouse (grapefruit), eggplant, endive, cranberry, gooseberry, hazel nuts, kiwifruit, almonds, amaranth, apricot, artichoke, avocado, blackberry, cashew nut, cherry, clementine, coconut, cantaloupes and includes their harvested goods, such as fruits and vegetables.

It is further generally preferred to use or employ the compound (I-1), (I-2) or (I-3) and the biological control agent selected from bacteria, in particular spore-forming bacteria, fungi or yeasts, protozoas, viruses, and entomopathogenic nematodes, and if applicable also the inoculant on broad acre crops, such as cotton, corn, soybean, cereals, canola, oil seed rape, sugar cane and rice.

Agrochemical formulations as mentioned herein, in particular solo-formulations and combined-formulations may generally include carrier, which is be understood as meaning a natural or synthetic, organic or inorganic substance which is mixed or combined with the active compounds for better applicability, in particular for application to plants or plant parts or seeds. The carrier which may be solid or liquid is generally inert and should be suitable for agricultural use. In a preferred embodiment, the carrier is a solid carrier. The formulations mentioned can be prepared in a manner known per se, for example by mixing the active the compound (I-1), (I-2) or (I-3) and the biological control agent selected from bacteria, in particular spore-forming bacteria, fungi or yeasts, protozoas, viruses, and entomopathogenic nematodes, and if applicable also the inoculant with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

Moreover, agrochemical formulations as mentioned herein may also generally include suitable solid or liquid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Moreover, agrochemical formulations as mentioned herein may also generally include suitable liquefied gaseous extenders or carriers are liquids which are gaseous at ambient temperature and under atmospheric pressure, for example aerosol propellants, such as butane, propane, nitrogen and carbon dioxide.

Moreover, agrochemical formulations as mentioned herein may also generally include suitable tackifiers, such as carboxymethylcellulose and natural and synthetic polymers in the form of powders, granules and latices, such as gum arabic, polyvinyl alcohol, polyvinyl acetate, or else natural phospholipids, such as cephal ins and lecithins and synthetic phospholipids can be used in the formulations. Other possible additives are mineral and vegetable oils and waxes, optionally modified.

Moreover, agrochemical formulations as mentioned herein may also generally include extender. If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

In one embodiment, an agrochemical formulation such as a solo-formulation or a combined-formulation comprises at least one of the following solvents selected from the group consisting of water, ketones, such as acetone, dimethylformamide and dimethyl sulphoxide.

In a further embodiment, an agrochemical formulation such as a solo-formulation or a combined-formulation comprises at least one of the following solvents selected from the group consisting of water, ketones, such as acetone, dimethylformamide and dimethyl sulphoxide; and further comprises an emulsifier selected from the group consisting of alkylaryl polyglycolether.

Moreover, agrochemical formulations as mentioned herein may also generally include additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention. It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

Moreover, agrochemical formulations as mentioned herein may also generally include other additional components, for example protective colloids, binders, adhesives, thickeners, thixotropic substances, penetrants, stabilizers, sequestering agents, complex formers.

Agrochemical formulations as mentioned herein can be used in form of aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microcncapsulations in polymeric substances and in coating materials for seed, and also ULV cold-fogging and warm-fogging formulations.

The combinations according to the invention do not only comprise ready-to-use formulations which can be applied with suitable apparatus to the plant or the seed, but also commercial concentrates which have to be diluted with water prior to use.

It is preferred that the composition containing a compound (I-1), (I-2) or (I-3) and the at least one biological control agent selected from bacteria, in particular spore-forming bacteria, fungi or yeasts, protozoas, viruses, and entomopathogenic nematodes, and optionally an inoculant according to the invention is formulated in a single, stable solution, or emulsion, or suspension. For solutions, the compound (I-1), (I-2) or (I-3) is dissolved in a suitable solvent before the biological control agent is added.

Suitable solvents are liquid and include petroleum based aromatics, such as xylene, toluene or alkylnaphthalenes, aliphatic hydrocarbons, such as cyclohexane or paraffins, for example petroleum fractions, mineral and veizetable oils, alcohols, such as butanol or glycol as well as their ethers and esters, ketones, such as methyl ethyl ketone, methyl isobutyl ketone or cyclohcxanone, strongly polar solvents, such as dimethylformamide and dimethyl sulphoxide. For emulsions and suspensions, the solvent is water.

In one embodiment, the compound (I-1), (I-2) or (I-3) and the at least one biological control agent selected from bacteria, in particular spore-forming bacteria, fungi or yeasts, protozoas, viruses, and entomopathogenic nematodes, and optionally the inoculant, are suspended in separate solvents and mixed at the time of application.

In a preferred embodiment the compound (I-1), (I-2) or (I-3) and the at least one biological control agent selected from bacteria, in particular spore-forming bacteria, fungi or yeasts, protozoas, viruses, and entomopathogenic nematodes, and optionally the inoculant are combined in a ready-to-use formulation that exhibits a shelf-life of at least two years. In use, the liquid can be sprayed or atomized foliarly or in-furrow at the time of planting the plant. The liquid composition can be introduced to the soil before germination of the seed or directly to the soil in contact with the roots by utilizing a variety of techniques including, but not limited to, drip irrigation, sprinklers, soil injection or soil drenching.

Optionally, stabilizers and buffers can be added, including alkaline and alkaline earth metal salts and organic acids, such as citric acid and ascorbic acid, inorganic acids, such as hydrochloric acid or sulfuric acid. Biocides can also be added and can include formaldehydes or formaldehyde-releasing agents and derivatives of benzoic acid, such as p-hydroxybenzoic acid.

In some embodiments, the terms alkane, alkyl, alkene, alkenyl, alkine, alkinyl, aryl when mentioned herein refer to groups containing $C_1$-$C_{20}$, $C_1$-$C_8$ or $C_1$-$C_6$ carbon atoms. Similarly, heteroaryl and other functional groups comprising alkyl, alkenyl, alkinyl or aryl, such as ketones, ethers, amines, etc., may contain $C_1$-$C_{20}$, $C_1$-$C_8$ or $C_1$-$C_6$ carbon atoms. Of course, combinations which are contrary to the law of nature (e.g., $C_2$-aryl) are excluded. The skilled person is well aware which combinations have to be excluded based on his or her expertise. In some embodiments, the term "poly" refers to units of 2-50000, 2-5000, 2-500, 2-50, 5-500, 50-500, 5-50 subunits.

In the agrochemical formulations or in the use forms of the compound (I-1), (I-2) or (I-3) and the biological control agent selected from bacteria, in particular spore-forming bacteria, fungi or yeasts, protozoas, viruses, and entomopathogenic nematodes, and or the inoculant, there may be additionally at least one further active compound present. Such active compounds may be insecticides, attractants, sterilants, bactericides, acaricides, nematicides, fungicides, uowth regulators, herbicides, fertilizers, safeners and semiochemicals. In one embodiment, the solid or liquid agrochemical formulations or use forms as mentioned before, may further contain functional agents capable of protecting seeds from the harmful effects of selective herbicides such as activated carbon, nutrients (fertilizers), and other agents capable of improving the germination and quality of the products or a combination thereof.

Conventional seeds which can be treated according to the invention are seeds of any plant variety employed in agriculture, in the greenhouse, in forests or in horticulture or in vineyards and include horticultural and broad acre crops. In particular, this takes the form of seed of cereals (such as wheat, barley, rye, (riticale, millet, oats), maize (corn), cotton, soybean, rice, potatoes, sunflowers, beans, coffee, beets (e.g. sugar beets and fodder beets), peanuts, oilseed rape, poppies, olives, coconuts, cacao, sugar cane, tobacco, vegetables (such as tomatoes, cucumbers, onions and lettuce), lawn and ornamental plants (also see below). The treatment of seeds of cotton, soybean, rape, cereals (such as wheat, barley, rye, triticale, and oats), maize (corn), beets, potatoes and rice is of particular importance.

Transgenic seeds containing at least one heterologous gene which allows the expression of a polypeptide or protein having insecticidal properties are particularly preferred to be treated according to the invention. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

The compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant according to the invention can be formulated as a solo-agrochemical formulation or a combined-agrochemical formulation with the aim to be sufficiently stable so that the treatment of the plants, plant parts, seeds, harvested fruits and vegetables does not cause any damage.

However, the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant can also be applied directly, that is to say without comprising further components and without having been diluted.

In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant is applied to the seed and/or the amount of further additives is chosen in such a way that the germination of the seed is not adversely affected, or that the resulting plant is not damaged.

Agrochemical formulations for treating seeds (seed dressing formulations) according to the invention are solutions, emulsions, suspensions, powders, foams, slurries or other coating materials for seed, and also ULV formulations (cf. U.S. Pat. No. 4,272,417, U.S. Pat. No. 4,245,432, U.S. Pat. No. 4,808,430, U.S. Pat. No. 5,876,739, US 2003/0176428, WO 2002/080675, WO 2002/028186).

Such seed dressing formulations are prepared in a known manner by mixing the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant with customary additives, such as, for example, customary extenders and also solvents or diluents, colorants, wetting agents, dispersants, emulsifiers, defoamers, preservatives, secondary thickeners, adhesives, gibberellins and water as well.

Suitable colorants that may be present in the seed dressing, formulations include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1.

Suitable wetting agents that may be present in the seed dressing formulations include all substances which promote wetting and are customary in the formulation of active agrochemical substances. With preference it is possible to use alkylnaphthalene-sulphonates, such as diisopropyl- or diisobutylnaphthalene-sulphonates.

Suitable dispersants and/or emulsifiers that may be present in the seed dressing formulations include all nonionic, anionic, and cationic dispersants which are customary in the formulation of active agrochemical substances. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers and tristyrylphenol polyglycol ethers, and their phosphated or sulphated derivatives. Particularly suitable anionic dispersants are lignosulphonates, polyacrylic salts, and arylsulphonate-formaldehyde condensates.

Defoamers that may be present in the seed dressing formulations include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof.

Preservatives that may be present in the seed dressing formulation include all compounds which can be used for such purposes in agrochemical compositions. By way of example, mention may be made of dichlorophen and benzyl alcohol hemiformal.

Secondary thickeners that may be present in the seed dressing formulations include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations are preferably the gibberellins A1, A3 (=gibberellic acid), A4 and A7; particular preference is given to using gibberellic acid. The gibberellins are known (Wegler "Chemie der Pflanzenschutz-und Schädlingsbekämpfungsmittel" [Chemistry of Crop Protection Agents and Pesticides], Vol. 2, Springer Verlag, 1970, pp. 401-412).

The seed dressing formulations can be used directly or after dilution with water beforehand to treat seed of any of a very wide variety of types or transgenic plants. When the latter seeds are used, synergistic effects may also arise in interaction with the substances formed by expression.

Suitable mixing equipment for treating seed with the seed dressing formulations or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

According to the present invention, the seeds are substantially uniformly coated with one or more layers of the compound (I-1), (I-2) or (I-3), preferably compound (I-3) and/or the at least one biological control agent selected from bacteria, in particular spore-forming bacteria, fungi or yeasts, protozoas, viruses, and entomopathogenic nematodes, and optionally the inoculant using conventional methods of mixing, spraying or a combination thereof through the use of treatment application equipment that is specifically, designed and manufactured to accurately, safely, and efficiently apply seed treatment products to seeds. Such equipment uses various types of coating technology such as rotary coaters, drum coaters, fluidized bed techniques, spouted beds, rotary mists or a combination thereof. Liquid seed treatments such as those of the present invention can be applied via either a spinning "atomizer" disk or a spray nozzle which evenly distributes the seed treatment onto the seed as it moves though the spray pattern. Preferably, the seed is then mixed or tumbled for an additional period of time to achieve additional treatment distribution and drying. The seeds can be primed or unprimed before coating with the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant to increase the uniformity of germination and emergence. In an alternative embodiment, a dry powder formulation can be metered onto the moving seed and allowed to mix until completely distributed.

The seeds may be coated via a batch or continuous coating process. In a continuous coating embodiment, continuous flow equipment simultaneously meters both the seed flow and the seed treatment products. A slide gate, cone and orifice, seed wheel, or weighing device (belt or diverter) regulates seed flow. Once the seed flow rate through treating equipment is determined, the flow rate of the seed treatment is calibrated to the seed flow rate in order to deliver the desired dose to the seed as it flows through the seed treating equipment. Additionally, a computer system may monitor the seed input to the coating machine, thereby maintaining a constant flow of the appropriate amount of seed.

In a batch coating embodiment, batch treating equipment weighs out a prescribed amount of seed and places the seed into a closed treating chamber or bowl where the corresponding dose of seed treatment is then applied. This batch is then dumped out of the treating chamber in preparation for the treatment of the next batch. With computer control systems, this batch process is automated enabling it to continuously repeat the batch treating process.

In either embodiment, the seed coating machinery can optionally be operated by a programmable logic controller that allows various equipments to be started and stopped without employee intervention. The components of this system are commercially available through several sources such as Gustafson Equipment of Shakopee, Minn.

If planted, any plant seed capable of germinating to form a plant that is susceptible to attack by insects, mites nematodes and/or pathogenic fungi can be treated in accordance with the invention. Particularly suitable convential (i.e. not being a transgenic seeds) or transgenic seeds are those of cole crops, vegetables (in particular the vegetables as mentioned herein as being horticultural crops), fruits (in particular the vegetables as mentioned herein as being horticultural crops), trees, fiber crops, oil crops, tuber crops, coffee, flowers, legume, cereals, as well as other plants of the monocotyledonous and dicotyledonous species. Preference is given to seeds of horticultural crops and of broad acre crops as mentioned herein. In particular, among those crops, seeds to be coated include soybean, cotton, corn, peanut, tobacco, grasses, wheat, barley, lye, sorghum, rice, rapeseed, sugar beet, sunflower, tomato, pepper, bean, lettuce, potato, and carrot seeds.

Additionally, if the seed treatment is done with transgenic seeds, then the plants emerging from these seeds are capable of the expression of a protein directed against pests and pathogens. By treatment of such seed with the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant certain pests and/or phytopathogens can already be controlled by expression of the, for example, insecticidal protein, and it is additionally surprising that a synergistic activity supplementation occurs when the compound (I-1), (I-2) or (I-3) and the biological control agents are used or employed for seed treatment, thereby improving still further the effectiveness of the protection from pest and pathogen infestation.

The agricultural pests and pathogens to be controlled when the compound (I-1), (I-2) or (I-3) and the biological control agents are used or employed according to the invention are given hereafter:

Agricultural Pests:

Order: Arthropoda: From the class of the Arachnida, for example *Acarus* spp., *Aceria sheldoni, Aculops* spp. *Aculus* spp., *Amblyomma* spp., *Amphitetranychus viennensisArgas* spp., *Boophilus* spp., *Brevipalpus* spp., *Bryobia praetiosa, Centruroides* spp., *Chorioptes* spp., *Dermanyssus gallinae, Dermatophagoides pteronyssius, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp.; *Vaejovis* spp., *Vasates lycopersici*.

From the order of the Anoplura (Phthiraptera), for example, *Damalinia* spp., *Haematopinus* spp., *Linognathus* spp., *Pediculus* spp., *Ptirus pubis, Trichodectes* spp.

From the order of the Chilopoda, for example. *Geophilus* spp., *Scutigera* spp.

From the order of the Coleoptera, for example, *Acalymma vittatum, Acanthoscelides obtectus, Adoretus* spp., *Agelastica alni, Agriotes* spp. *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hvpera postica, Hypothenemus* spp., *Lachnosterna consanguinea, Lema* spp., *Leptinotarsa decemlineata, Leucoptera* spp., *Lisso-rhoptrus oryzophilus, Lixus* spp., *Luperodes* spp., *Lyctus* spp.,

*Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Prostephanus truncates*, *Psylliodes* spp., *Ptinus* spp., *Rhizobius ventralis*, *Rhizopertha dominica*, *Sitophilus* spp., *Sphenophorus* spp., *Stegobium paniceum*, *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulutus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Chrysops* spp., *Cochliomyia* spp., *Contarinia* spp. *Cordylobia anthropophaga*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp. *Lucilia* spp., *Lutzomia* spp., *Mansonia* spp., *Musca* spp., *Nezara* spp., *Oestrus* spp., *Oscinella frit*, *Pegomyia* spp., *Phlebotomus* spp., *Phorbia* spp., *Phormia* spp., *Prodiplosis* spp., *Psila rosae*, *Rhagoletis* spp., *Sarcophaga* spp., *Simulium* spp, *Stomoxys* spp., *Tabanus* spp., *Tannia* spp., *Tetanops* spp., *Tipula* spp.

From the order of the Heteroptera, for example, *Anasa tristis*, *Antestiopsis* spp., *Boisea* spp., *Blissus* spp., *Calocoris* spp., *Campylomma livida*, *Caveleritis* spp., *Cimex* spp., *Cimex lectularius*. *Cimex hemipterus*, *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrates*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeztrodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulant*, *Hyalopterus arundinis*, *Icerya* spp., *Idiocerus* spp., *Idioscopus* spp., *Lao-delphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrines maidis*, *Phenacoccus* spp., *Phloeomyzus passerinii*, *Phorodon humuli*, *Phylloxera* spp., *Pinnaspis aspidistras*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Hymenoptera, for example, *Acromyrmex* spp., *Athalia* spp., *Atta* spp., *Diprion* spp., *Hoplocampa* spp., *Lasius* spp., *Monomorium pharaonis*, *Solenopsis invicta*, *Tapinoma* spp., *Vespa* spp.

From the order of the Isopoda, for example, *Armadillidium vulgare*, *Oniscus asellus*, *Porcellio scaber*.

From the order of the Isoptera, for example, *Coptotermes* spp., *Cornitermes cumulans*, *Cryptotermes* spp., *Incisitermes* spp., *Microtermes obesi*, *Odontotermes* spp., *Reticulitermes* spp.

From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Monica testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp. *Spargan-*

*othis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

From the order of the Orthoptera, for example, *Acheta domesticuos, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

From the order of the Siphonaptera, for example, *Ceratophyllus* spp., *Ctenocephalides* spp., *Tunga penetrans, Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Zygentoma (=Thysanura), for example, *Lepisma saccharina, Thermobia domestica,* or *Lepisma saccharina, Thermobia domestica,*

Order: Mollusca: From the class of the Bivalvia, for example, *Dreissena* spp. From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

Order: Plathelminthes, Nematodes (animal parasites): From the class of the Helminths, for example, *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria hancrofti.*

Order: Nematodes (plant parasites, phytoparasites): From the group of the phytoparasitic nematodes, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp., Subphylum: Protozoa such as *Eimeria.*

Some phytopathogens of fungal diseases which can be treated according to the invention may be mentioned by way of example, but not by way of limitation:

Diseases caused by powdery mildew pathogens, such as, for example, *Blumeria* species, such as, for example, *Blumeria graminis; Podosphaera* species, such as, for example, *Podosphaera leuco-tricha; Sphaerotheca* species, such as, for example, *Sphaerotheca fuliginea; Uncinula* species, such as, for example, *Uncinula necator;*

Diseases caused by rust disease pathogens, such as, for example, *Gymnosporangium* species, such as, for example, *Gymnosporangium sabinae; Hemileia* species, such as, for example, *Hemileia vastatrix; Phakopsora* species, such as, for example, *Phakopsora pachyrhizi* and *Phakopsora meibomiae; Puccinia* species, such as, for example, *Puccinia recondita* or *Puccinia triticina; Uromyces* species, such as, for example, *Uromyces appendiculatus;*

Diseases caused by pathogens from the group of the Oomycetes, such as, for example, *Albugo* species, such as, for example, *Albugo candida; Bremia* species, such as, for example, *Bremia lactucae; Peronospora* species, such as, for example, *Peronospora piii* or *P. brassicae; Phytophthora* species, such as, for example *Phytophthora infestans; Plasmopara* species, such as, for example, *Plasmopara viticola; Pseudoperonospora* species, such as, for example, *Pseudoperonospora humuli* or *Pseudoperonospora cubensis; Pythium* species, such as, for example, *Pythium ultimum;*

Leaf blotch diseases and leaf wilt diseases caused, for example, by *Alternaria* species, such as, for example, *Alternaria solani; Cercospora* species, such as, for example, *Cercospora beticola; Cladiosporium* species, such as, for example, *Cladiosporium cucumerinum; Cochliobolus* species, such as, for example, *Cochliobolus sativus* (conidia form: *Drechslera*, Syn: *Helminthosporium*) and *Cochliobolus miyabeanus; Colletotrichum* species, such as, for example, *Colletotrichum lindemuthanium; Cycloconium* species, such as, for example, *Cycloconium oleaginum; Diaporthe* species, such as, for example, *Diaporthe citri; Elsinoe* species, such as, for example, *Elsinoe fawcettii; Gloeosporium* species, such as, for example, *Gloeosporium laeticolor; Glomerella* species, such as, for example, *Glomerella cingulata; Guignardia* species, such as, for example, *Guignardia bidwelli; Leptosphaeria* species, such as, for example, *Leptosphaeria maculans* and *Leptosphaeria nodorum; Magnaporthe* species, such as, for example, *Magnaporthe grisea; Microdochium* species, such as, for example, *Microdochium nivale; Mycosphaerella* species, such as, for example, *Mycosphaerella graminicola, Mycosphaerella arachidicola* and *Mycosphaerella fijiensis; Phaeosphaeria* species, such as, for example, *Phaeosphaeria nodorum; Pyrenophora* species, such as, for example, *Pyrenophora teres* and *Pyrenophora tritici repentis; Ramularia* species, such as, for example, *Ramularia collo-cygni* and *Ramularia areola; Rhynchosporium* species, such as, for example, *Rhynchosporium secalis; Septoria* species, such as, for example, *Septoria apii* and *Septoria lycopersici; Typhula* species, such as, for example, *Typhula incarnata; Venturia* species, such as, for example, *Venturia inaequalis;*

Root, sheath and stem diseases caused, for example, by *Corticium* species, such as, for example, *Corticium graminearum; Fusarium* species, such as, for example, *Fusarium oxysporum; Gaeumannomyces* species, such as, for example, *Gaeumannomyces graminis; Rhizoctonia* species, such as, for example *Rhizoctonia solani; Sarocladium* species, such as, for example, *Sarocladium oryzae; Sclerotium* species, such as, for example, *Sclerotium oryzae; Tapesia* species, such as, for example, *Tapesia acuformis; Thielaviopsis* species, such as, for example, *Thielaviopsis basicola;*

Ear and panicle diseases (including maize cobs) caused, for example, by *Alternaria* species, such as, for example, *Alternaria* spp.; *Aspergillus* species, such as, for example, *Aspergillus flavus; Cladosporium* species, such as, for example, *Cladosporium cladosporioides; Claviceps* species, such as, for example, *Claviceps purpurea; Fusarium* species, such as, for example, *Fusarium culmorum; Gibberella* species, such as, for example, *Gibberella zeae; Monographella* species, such as, for example, *Monographella nivalis; Septoria* species, such as for example, *Septoria nodorum*; Seed- and soil-borne decay, mould, wilt, rot and damping-off diseases; caused, for example, by *Alternaria* diseases caused for example by *Alternaria brassicicola; Aphanomyces* diseases caused for example by *Aphanomyces euteiches; Ascochyta* diseases caused for example by *Ascochyta lentis; Aspergillus* diseases caused for example by *Aspergillus flavus; Cladosporium* diseases caused for example by *Cladosporium herbarum; Cochliobolus* diseases caused for example by *Cochliobolus sativus*; (*Conidiaform: Drechslera, Bipolaris* Syn: *Helminthosporium*); *Colletotrichum* diseases caused for example by *Colletotrichum coccodes; Fusarium* diseases caused for example by *Fusarium culmorum; Gibberella* diseases caused for example by *Gibberella zeae; Macrophomina* diseases caused for example by *Macrophomina phaseolina; Microdochium* diseases caused for example by *Microdochium nivale; Monographella* diseases caused for example by *Monographella nivalis; Penicillium* diseases caused for example by *Penicillium expansum; Phoma* diseases caused for example by *Phoma lingam; Phomopsis* diseases caused for example by *Phomopsis sojae; Phytophthora* diseases caused for example by *Phytophthora cactorum; Pyrenophora* diseases caused for example by *Pyrenophora graminea; Pyricularia* diseases caused for example by *Pyricularia oryzae; Pythium* diseases caused for example by *Pythium ultimum; Rhizoetonia* diseases caused for example by *Rhizoctonia solani; Rhizopus* diseases caused for example by *Rhizopus oryzae; Sclerotium* diseases caused for example by *Sclerotium rolfsii; Septoria* diseases caused for example by *Septoria nodorum; Typhula* diseases caused for example by *Typhula incarnata; Verticillium* diseases caused for example by *Verticillium dahliae*;

Diseases caused by smut and bunt fungi, such as, for example, *Sphacelotheca* species, such as, for example, *Sphacelotheca reiliana; Tilletia* species, such as, for example, *Tilletia caries; Tilletia controversa, Urocystis* species, such as, for example, *Urocystis occulta; Ustilago* species, such as, for example, *Ustilago nuda; Ustilago nuda tritici*;

Fruit rot caused, for example, by *Aspergillus* species, such as, for example, *Aspergillus flavus; Botrytis* species, such as, for example, *Botrytis cinerea; Penicillium* species, such as, for example, *Penicillium expansum* and *Penicillium purpurogenum; Rhizopus* species, such as, for example, *Rhizopus stolonifer; Sclerotinia* species, such as, for example. *Sclerotinia sclerotiorum; Verticilium* species, such as, for example, *Verticilium alboatrum*;

Seed- and soil-borne rot and wilt diseases, and also diseases of seedlings, caused, for example, by *Alternaria* species, such as, for example, *Alternaria brassicicola; Aphanomyces* species, such as, for example, *Aphanomyces euteiches; Ascochyta* species, such as, for example, *Ascochyta lentis; Aspergillus* species, such as, for example, *Aspergillus flavus; Cladosporium* species, such as, for example, *Cladosporium herbarum; Cochliobolus* species, such as, for example, *Cochliobolus sativus* (*conidiaform: Drechslera, bipolaris* syn: *Helminthosporium*); *Colletotrichum* species, such as, for example, *Colletotrichum coecodes; Fusarium* species, such as, for example, *Fusarium culmorum; Gibberella* species, such as, for example, *Gibberella zeae; Macrophomina* species, such as, for example, *Macrophomina phaseolina; Microdochium* species, such as, for example. *Microdochium nivale; Monographella* species, such as, for example, *Monographella nivalis; Penicillium* species, such as, for example, *Penicillium expansum; Phoma* species, such as, for example, *Phoma lingam; Phomopsis* species, such as, for example, *Phomopsis sojae; Phytophthora* species, such as, for example, *Phytophthora cactorum; Pyrenophora* species, such as, for example, *Pyrenophora graminea; Pyricularia* species, such as, for example, *Pyricularia oryzae Pythium* species, such as, for example, *Pythium ultimum; Rhizoctonia* species, such as, for example. *Rhizoctonia solani; Rhizopus* species, such as, for example, *Rhizopus oryzae; Sclerotium* species, such as, for example, *Sclerotium rolfsii; Septoria* species, such as, for example, *Septoria nodorum; Typhula* species, such as, for example, *Typhula incarnate; Verticillium* species, such as, for example, *Verticillium dahliae*;

Cancerous diseases, galls and witches' broom caused, for example, by *Nectria* species, such as, for example, *Nectria galligena*;

Wilt diseases caused, for example, by *Monilinia* species, such as, for example, *Monilinia laxa*; Deformations of leaves, flowers and fruits caused, for example, by *Exobasidium* species, such as, for example, *exobasidium vexans; Taphrina* species, such as, for example, *Taphrina deformans*;

Degenerative diseases of woody plants caused, for example, by *Esca* species, such as, for example, *Phaemoniella clamydospora* and *Phaeoacremonium aleophilum* and *Fomitiporia mediterranea; Ganoderma* species, such as, for example, *Ganoderma boninense; Rigidoporus* species, such as, for example, *Rigidoporus lignosus*;

Club root diseases caused, for example, by *Plasmodiophora* species, such as, for example, *Plasmodiophora brassicae*;

Diseases of flowers and seeds caused, for example, by *Botrytis* species, such as, for example, *Botrytis cinerea*;

Diseases of plant tubers caused, for example, by *Rhizoctonia* species, such as, for example, *Rhizoctonia solani; Helminthosporium* species, such as, for example, *Helminthosporium solani*;

Diseases caused by bacteriopathogens, such as, for example, *Xanthomonas* species, such as, for example. *Xanthomonas campestris* pv. *oryzae; Pseudomonas* species, such as, for example, *Pseudomonas syringae* pv, *lachrymans; Erwinia* species, such as, for example, *Erwinia amylovora*.

Preference is given to controlling the following diseases of soy beans:

Fungal diseases on leaves, stems, pods and seeds caused, for example, by alternaria leaf spot (*Alternaria spec. atrans tenuissima*), anthraenose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stein canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stein decay, and damping-off (*Rhizoctonia solani*), sclerotinia stem decay (*Sclerotinia sclerotiorum*), sclerotinia Southern blight (*Selerotinia rolfsii*), thielaviopsis root rot (*Thielaviopsis basicola*).

It is also possible to control resistant strains of the organisms mentioned above.

In addition, the compound (I-1), (I-2) or (I-3) in combination with at least one biological control agent selected from bacteria, in particular spore-forming bacteria, fungi or yeasts, protozoas, viruses, and entomopathogenic nematodes, and optionally the inoculant as given herein can also exhibit very good antimycotic activity, in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *andouinii*. The list of these fungi by no means limits the mycotic spectrum which can be covered, but is only for illustration.

Furthermore, the compound (I-1), (I-2) or (I-3) in combination with at least one biological control agent selected from bacteria, in particular spore-forming bacteria, fungi or yeasts, protozoas, viruses, and entomopathogenic nematodes, and optionally the inoculant as given herein can also be used to reduce the contents of mycotoxins in plants and the harvested plant material and therefore in foods and animal feed stuff made therefrom. Especially but not exclusively the following mycotoxins can be specified: Deoxynivalenole (DON), Nivalenole, 15-Ac-DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalkaloides und Aflatoxines, which are caused for example by the following fungal diseases: *Fusarium* spec., like *Fusarium acuminatum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

Moreover, plants and plant parts which are mentioned herein are all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include crop material and vegetative and generative propagation material, for example cuttings, tubers, rhizomes, slips and seeds.

As has already been mentioned above, all plants and their parts may be treated in accordance with the invention. In a preferred embodiment, plant species and plant varieties, and their parts, which grow wild or which are obtained by traditional biological breeding methods such as hybridization or protoplast fusion are treated. In a further preferred embodiment, transgenic plants and plant varieties which have been obtained by recombinant methods, if appropriate in combination with traditional methods (genetically modified organisms), and their parts are treated. The term "parts" or "parts of plants" or "plant parts" has been explained hereinabove. Plants of the plant varieties which are in each case commercially available or in use are especially preferably treated in accordance with the invention. Plant varieties are understood as meaning plants with novel traits which have been bred both by traditional breeding, by mutagenesis or by recombinant DNA techniques. They may take the form of varieties, races, biotypes and genotypes.

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term useful plants as used in the present context refers to crop plants which are employed as plants for obtaining foodstuffs, feedstuffs, fuels or for industrial purposes.

The useful plants which can be improved with by using or employing the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant, include for example the following types of plants: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; *Lauraceae*, for example avocado, *Cinnamomum*, camphor, or else plants such as tobacco, nuts, coffee, aubergine, sugar cane, tea, pepper, grapevines, hops, bananas, latex plants and ornamentals, for example flowers, shrubs, deciduous trees and coniferous trees.

The following plants are considered to be particularly suitable target crops for using or employing the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potato and apple.

Examples of trees are: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved in accordance with the method according to the invention are: from the tree species *Aesculus*: *A. hippocastanum*A. *pariflora*, *A. carnea*: from the tree species *Platanus*: *P. aceriflora, P. occidentalis, P. racemosa*; from the tree species *Picea*: *P. abies*; from the tree species *Pinus*: *P. radiata, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus*: *E. grandis, E. globulus, E. camadentis, E. niiens, E. obliqua, E. regnans, E. pilularus*.

Especially preferred trees which can be improved in accordance with the method according to the invention are: from the tree species *Pinus*: *P. radiata, P. ponderosa, P. contorta, P. sylvestre, P. strobes*; from the tree species *Eucalyptus*: *E. grandis, E. globulus, E. camadentis*.

Very particularly preferred trees which can be improved in accordance with the method according to the invention are: horse chestnut, Platanaceae, linden tree, maple tree.

The present invention can also be applied to any turf grasses, including cool-season turf grasses and warm-season turf grasses. Examples of cold-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German mixed bentgrass (*Agrostis* spp. including *Agrostis tenuis* Sibth., *Agrostis canina* L., and *Agrostis palustris* Huds.), and redtop (*Agrostis alba* L.); fescues (*Festuca* spp.), such as red fescue (*Festuca rubra* L. spp. rubra), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festuca capillata* Lam.), tall fescue (*Festuca arundinacea* Schreb.) and meadow fescue (*Festuca elanor* L.); ryegrasses (*Lolium* spp.), such as annual ryegrass (*Lolium multiflorum* Lam.), perennial ryegrass (*Lolium perenne* L.) and Italian ryegrass (*Lolium multiflorum* Lam.); and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turf grasses are beachgrass (*Ammophila breviligulata* Fern.), smooth bromegrass (*Bromus inermis* Leyss.), cattails such as timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm-season turf grasses are Bermuda grass (*Cynodon* spp. L. C. Rich), zoysia grass (*Zoysia* spp. Willd.), St. Augustine grass (*Stenotaphrum secundatum* Walt Kuntze), centipede grass (*Eremochloa ophiuroides* Munro Hack.), carpetgrass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelin.), blue grama (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Cool-season turf grasses are generally preferred for the use according to the invention. Especially preferred are bluegrass, benchgrass and redtop, fescues and ryegrasses. Bentgrass is especially preferred.

It is understood that if not mentioned otherwise all references to plant, plant parts, seeds, plants emerging from the seed includes conventional or transgenic plant, plant parts, seeds, plants emerging from the seed. Transgenic (genetically modified) plants are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by down regulating or silencing other gene(s) which are present in the plant (using for example, antisense technology, co-suppression technology or RNA interference-RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), using or employing the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant the treatment according to the invention may also result in super-additive ("synergistic") effects. Thus, for example, by using or employing the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant in the treatment according to the invention, reduced application rates and/or a widening of the activity spectrum and/or an increase in the activity better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates of the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant in the treatment according to the invention may also have a strengthening effect in plants. The defense system of the plant against attack by unwanted phytopathogenic fungi and/or microorganisms and/or viruses is mobilized. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these phytopathogenic fungi and/or microorganisms and/or viruses, Thus, by using or employing the compound (I-1), (I-2) or (I-3), preferably compound (I-3) and the at least one biological control agent selected from bacteria, in particular spore-forming bacteria, fungi or yeasts, protozoas, viruses, and entomopathogenic nematodes, and optionally the inoculant in the treatment according to the invention, plants can be protected against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of., for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphare synthase (EPSPS). Examples of such EPSPS genes are the AroA gene (mutant CT7) of the bacterium *Salmonella typhimurium*, the CP4 gene of the bacterium *Agrobacterium* sp, the genes encoding a Petunia EPSPS, a Tomato EPSPS, or an *Eleusine* EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is described in WO 1996/033270. Other imidazolinone-tolerant plants are also described. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) An insecticidal crystal protein from *Bacillus thuringiensis* or an insecticidal portion thereoL such as the insecticidal crystal proteins listed online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Aa, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or
3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;
5) an insecticidal secreted protein from *Bacillus thuringiensis* or *Bacillus cereus*, or an insecticidal portion thereof, such as the vegetative insecticidal (VIP) proteins listed at: http:www.lifesci.sussex.ac.uk/home/Neil_Crickmore/Bt/vip.html. e.g. proteins from the VIP3Aa protein class; or
6) secreted protein from *Bacillus thuringiensis* or *Bacillus cereus* which is insecticidal in the presence of a second secreted protein from *Bacillus thuringiensis* or *B. cereus*, such as the binary toxin made up of the VIP IA and VIP2A proteins; or
7) hybrid insecticidal protein comprising parts from different secreted proteins from *Bacillus thuringiensis* or *Bacillus cereus*, such as a hybrid of the proteins in 1) above or a hybrid of the proteins in 2) above; or
8) protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Plants or plant cultivars (obtained by plant biotechnology methods such as genetic engineering) which may also be treated according to the invention are nematode-resistant transgenic plants, i.e. plants made resistant to attack by certain target nematode. Such plants can be obtained by genetic transformation, or by selection of plants containing a mutation imparting such insect resistance Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants
b. plants which contain a stress tolerance enhancing transgene capable of reducing the expression and/or the activity of the poly(ADP-ribose)glycohydrolase (PARG) encoding genes of the plants or plants cells.
c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1,4-glucans, plants producing alternan, 3) transgenic plants which produce hyaluronan.

Plants or plant cultivars (that can be obtained by plant biotechnology methods such as genetic engineering) which may also be treated according to the invention are plants, such as cotton plants, with altered fiber characteristics. Such plants can be obtained by genetic transformation or by selection of plants contain a mutation imparting such altered fiber characteristics and include:

a) Plants, such as cotton plants, containing an altered form of cellulose synthase genes, b) Plants, such as cotton plants, containing an altered form of rsw2 or rsw3 homologous nucleic acids, c) Plants, such as cotton plants, with increased expression of sucrose phosphate synthase, d) Plants, such as cotton plants, with increased expression of sucrose synthase, e) Plants, such as cotton plants, wherein the timing of the plasmodesmatal gating at the basis of the fiber cell is altered, e.g. through downregulation of fiberselective β1,3-glucanase, f) Plants, such as cotton plants, having fibers with altered reactivity, e.g. through the expression of N-acteylglucosaminetransferase gene including nodC and chitin-synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content, b) Plants such as oilseed rape plants, producing oil having a low linolenic acid content, c) Plant such as oilseed rape plants, producing oil having a low level of saturated fatty acids.

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtrat (for example maize), StarLink® (for example maize), Bollgard® (cotton), Nucotn® (cotton), Nucotn 33B☐ (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO 06/128569); Event 1143-51B (cotton, insect control, not deposited, described in WO 06/128570); Event 1445 (cotton, herbicide tolerance, not deposited, described in US-A 2002-120964 or WO 02/034946); Event 17053 (rice, herbicide tolerance, deposited as PTA-9843, described in WO 10/117737); Event 17314 (rice, herbicide tolerance, deposited as PTA-9844, described in WO 10/117735); Event 281-24-236 (cotton, insect control—herbicide tolerance, deposited as PTA-6233, described in WO 05/103266 or US-A 2005-216969); Event 3006-210-23 (cotton, insect control—herbicide tolerance, deposited as PTA-6233, described in US-A 2007-143876 or WO 05/103266); Event 3272 (corn, quality trait, deposited as PTA-9972, described in WO 06/098952 or US-A 2006-230473); Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO 11/075595); Event 5307 (corn, insect control, deposited as ATCC PTA-9561, described in WO 10/077816); Event ASR-368 (bent grass, herbicide tolerance, deposited as ATCC PTA-4816, described in US 2006-162007 or WO 04/053062); Event B16 (corn, herbicide tolerance, not deposited, described in US-A 2003-126634); Event BPS-CV127-9 (soybean, herbicide tolerance, deposited as NCIMB No. 41603, described in WO 10/080829); Event CE43-67B (cotton, insect control, deposited as DSM ACC2724, described in US 2009-217423 or WO 06/128573); Event CE44-69D (cotton, insect control, not deposited, described in US 2010-0024077); Event CE44-69D (cotton, insect control, not deposited, described in WO 06/128571); Event CE46-02A (cotton, insect control, not deposited, described in WO 06/128572); Event COT102 (cotton, insect control, not deposited, described in US 2006-130175 or WO 04/039986); Event COT202 (cotton, insect control, not deposited, described in US 2007-067868 or WO 05/054479); Event COT203 (cotton, insect control, not deposited, described in WO 05/054480); Event DAS40278 (corn, herbicide tolerance, deposited as ATCC PTA-10244, described in WO 11/022469); Event DAS-59122-7 (corn, insect control—herbicide tolerance, deposited as ATCC PTA 11384, described in US 2006-070139); Event DAS-59132 (corn, insect control—herbicide tolerance, not deposited, described in WO 09/100188); Event DAS68416 (soybean, herbicide tolerance, deposited as ATCC PTA-10442, described in WO 11/066384 or WO 11/066360); Event DP-098140-6 (corn, herbicide tolerance, deposited as ATCC PTA-8296, described in US 2009-137395 or WO 08/112019); Event DP-305423-1 (soybean, quality trait, not deposited, described in US 2008-312082 or WO 08/054747); Event DP-32138-1 (corn, hybridization system, deposited as ATCC PTA-9158, described in US-A 2009-0210970 or WO 09/103049); Event DP-356043-5 (soybean, herbicide tolerance, deposited as ATCC PTA-8287, described in US 2010-0184079 or WO 08/002872); Event EE-1 (brinjal, insect control, not deposited, described in WO 07/091277); Event FI117 (corn, herbicide tolerance, deposited as ATCC 209031, described in US 2006-059581 or WO 98/044140); Event GA21 (corn, herbicide tolerance, deposited as ATCC 209033, described in US 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO 08/151780); Event GHB614 (cotton, herbicide tolerance, deposited as ATCC PTA-6878, described in US 2010-050282 or WO 07/017186); Event GJ11 (corn, herbicide tolerance, deposited as ATCC 209030, described in US 2005-188434 or WO 98/044140); Event GM RZ13 (sugar beet, virus resistance, deposited as NCIMB-41601, described in WO 10/076212); Event H7-1 (sugar beet, herbicide tolerance, deposited as NCIMB 41158 or NCIMB 41159, described in US 2004-172669 or WO 04/074492); Event JOPLIN1 (wheat, disease tolerance, not deposited, described in US 2008-064032); Event LL27 (soybean, herbicide tolerance, deposited as NCIMB41658, described in WO 06/108674 or US 2008-320616); Event LL55 (soybean, herbicide tolerance, deposited as NCIMB 41660, described in WO 06/108675 or US 2008-196127); Event LLcotton25 (cotton, herbicide tolerance, deposited as ATCC PTA-3343, described in WO 03/013224 or US-A 2003-097687); Event LLRICE06 (rice, herbicide tolerance, deposited as ATCC-23352, described in U.S. Pat. No. 6,468,747 or WO 00/026345); Event LLRICE601 (rice, herbicide tolerance, deposited as ATCC PTA-2600, described in US-A 2008-2289060 or WO 00/026356); Event LY038 (corn, quality trait, deposited as ATCC PTA-5623, described in US-A 2007-028322 or WO 05/061720); Event MIR162 (corn, insect control, deposited as PTA-8166, described in US-A 2009-300784 or WO 07/142840); Event MIR604 (corn, insect control, not deposited, described in US-A 2008-167456 or WO 05/103301); Event MON15985 (cotton, insect control, deposited as ATCC PTA-2516, described in US 2004-250317 or WO 02/100163); Event MON810 (corn, insect control, not deposited, described in US-A 2002-102582); Event MON863 (corn, insect control, deposited as ATCC PTA-2605, described in WO 04/011601 or US 2006-095986); Event MON87427 (corn, pollination control, deposited as ATCC PTA-7899, described in WO 11/062904); Event MON87460 (corn, stress tolerance, deposited as ATCC PTA-8910, described in WO 09/111263 or US 2011-0138504); Event MON87701 (soybean, insect control, deposited as ATCC PTA-8194, described in US 2009-130071 or WO 09/064652); Event MON87705 (soybean, quality trait—herbicide tolerance, deposited as ATCC PTA-9241, described in US 2010-0080887 or WO 10/037016); Event MON87708 (soybean, herbicide tolerance, deposited as ATCC PTA9670, described in WO 11/034,704); Event MON87754 (soybean, quality trait, deposited as ATCC PTA-9385, described in WO 10/024,976); Event MON87769 (soybean, quality trait, deposited as ATCC PTA-8911, described in US 2011-0067141 or WO 09/102873); Event MON88017 (corn, insect control—herbicide tolerance, deposited as ATCC PTA-5582, described in US 2008-028482 or WO 05/059103); Event MON88913 (cotton, herbicide tolerance, deposited as ATCC PTA-4854, described in WO 04/072235 or US 2006-059590); Event MON89034 (corn, insect control, deposited as ATCC PTA-7455, described in WO 07/140,256 or US 2008-260932); Event MON89788 (soybean, herbicide tolerance, deposited as ATCC PTA-6708, described in US-A 2006-282915 or WO 06/130436); Event MS11 (oilseed rape, pollination control—herbicide tolerance, deposited as ATCC PTA-850 or PTA-2485, described in WO 01/031042); Event MS8 (oilseed rape, pollination control—herbicide tolerance, deposited as ATCC PTA-730, described in WO 01/041558 or US-A 2003-188347); Event NK603 (corn, herbicide tolerance, deposited as ATCC PTA-2478, described in US-A 2007-292854); Event PE-7 (rice, insect control, not deposited, described in WO 08/114282); Event RF3 (oilseed rape, pollination control—herbicide tolerance, deposited as ATCC PTA-730, described in WO 01/041558 or US 2003-188347); Event RT73 (oilseed rape, herbicide tolerance, not deposited, described in WO 02/036831 or US-A 2008-070260); Event T227-1 (sugar beet, herbicide tolerance, not deposited, described in WO 02/44407 or US-A 2009-265817); Event T25 (corn, herbicide tolerance, not deposited, described in US 2001-029014 or WO 01/051654); Event T304-40 (cotton, insect control—herbicide tolerance, deposited as ATCC PTA-8171, described in US 2010-077501 or WO 08/122406); Event T342-142 (cotton, insect control, not deposited, described in WO 06/128568); Event TC1507 (corn, insect control—herbicide tolerance, not deposited, described in US 2005-039226 or WO 04/099447); Event VIP1034 (corn, insect control—herbicide tolerance, deposited as ATCC PTA-3925., described in WO 03/052073), Event 32316 (corn, insect control-herbicide tolerance, deposited as PTA-11507, described in WO 11/084632), Event 4114 (corn, insect control-herbicide tolerance, deposited as PTA-11506, described in WO 11/084621).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

The invention is illustrated by the following examples without restricting the scope of invention:

Formula for the Efficacy of the Combination of Two Compounds

The expected efficacy of a given combination of two compounds is calculated as follows (see Colby, S. R., "Calculating Synergistic and antagonistic Responses of Herbicide Combinations", Weeds 15, pp. 20-22, 1967):

X is the efficacy expressed in % mortality of the untreated control for test compound A at a concentration of m ppm or m g/ha, Y is the efficacy expressed in % mortality of the untreated control for test compound B at a concentration of n ppm or m g/ha, E is the efficacy expressed in % mortality of the untreated control using the combination of A and B at m and n ppm or m and n g/ha, $$E = X + Y - \frac{X \cdot Y}{100}.$$

if the observed insecticidal efficacy of the combination is higher than the one calculated as "E", then the combination of the two compounds is more than additive, i.e., there is a synergistic effect.

Example 1

*Myzus persicae*—Foliar Application

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. To produce a suitable preparation of a biological suspension the cells or spores are diluted with emulsifier-containing water to the desired concentration.

Cabbage leaves (Brassica oleracea) which are heavily infested by the Green peach aphid (Myzus persicae) are treated by being sprayed with the preparation of the active compound at the desired concentration.

After the specified period of time, mortality in % is determined. 100% means that all the aphids have been killed; 0% means that none of the aphids have been killed. The mortality values thus determined are recalculated using the Colby-formula.

The following combination of compound and biological showed a synergistic effect according to the invention:

TABLE 1-1

| Myzus persicae - Test | | | |
|---|---|---|---|
| Active ingredient/ biological control agent | Concentration g ai/ha | Mortality in % after $6^d$ | |
| Compound (I-3) | 100 g ai/ha | 90 | |
| Metschnikowia fructicola strain NRRL Y-30752, yeast cells | 892.5 g yeast cell preparation/ha ($=10^{13}$ cells/ha) | 0 | |
| | | obs.* | cal.** |
| Compound (I-3) + M. fructicola | 100 + 892.5 | 100 | 90 |

Myzus persicae—Test (Spray Application)

| Solvent: | 78.0 parts by weight acetone |
| | 1.5 parts by weight dimethylformamide |
| Emulsifier: | 0.5 parts by weight alkylarylpolyglycolether |

To produce a suitable preparation of active compound, 1 part by weight of active compound is mixed with the stated amount of solvent and emulsifier, and the concentrate is diluted with emulsifier-containing water to the desired concentration. To produce a suitable preparation of a biological suspension the cells or spores are diluted with emulsifier-containing water to the desired concentration.

Chinese cabbage (Brassica pekinesis) leaf—discs infected with all instars of the green peach aphid (Myzus persicae), are sprayed with a preparation of the active ingredient at the desired concentration.

After the specified period of time mortality in % is determined. 100% means that all aphids have been killed; 0% means that none of the aphids have been killed.

The following combinations of compound and biological showed a synergistic effect according to the invention:

TABLE 1-2

| Myzus persicae - Test | | | |
|---|---|---|---|
| Active ingredient/ biological control agent | Concentration g ai/ha | Mortality in % after $1^d$ | |
| Compound (I-3) | 20 | 0 | |
| Bacillus subtilis strain GB 03 (ATCC SD-1397) | 2000 g spore preparation/ha ($=3 \times 10^{12}$ spores/ha) | 0 | |
| | | obs.* | cal.** |
| Compound (I-3) + B. subtilis GB03 | 20 + 2000 | 80 | 0 |

TABLE 1-2-continued

| Myzus persicae - Test | | | |
|---|---|---|---|
| Active ingredient/ biological control agent | Concentration g ai/ha | Mortality in % after $1^d$ | |
| Bacillus thuringiensis subsp. aizawai, strain ABTS-1857, spores | 1000 g spore preparation/ha ($=8.1 \times 10^9$ spores/ha) | 0 | |
| | | obs.* | cal.** |
| Compound (I-3) + B. thuringiensis subsp. aizawai, strain ABTS-1857 | 20 + 1000 | 80 | 0 |
| Paecilomyces lilacinus strain 251 Accession No. 89/030550 | 5000 g spore preparation/ha ($=5 \times 10^{13}$ spores/ha) | 0 | |
| | | obs.* | cal.** |
| Compound (I-3) + Paecilomyces lilacinus strain 251 | 20 + 5000 | 70 | 0 |

Example 2

Phaedon cochleariae Larvae—Foliar Application

| Solvent: | 7 parts by weight of dimethylformamide |
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. To produce a suitable preparation of a spore suspension the spores are diluted with emulsifier-containing water to the desired concentration.

Cabbage leaves (Brassica oleracea) are treated by being sprayed with the preparation of the active compound of the desired concentration and are infested with larvae of the mustard beetle (Phaedon cochleariae) as long as the leaves are still moist.

After the specified period of time, mortality in % is determined. 100% means that all the beetle larvae have been killed; 0% means that none of the beetle larvae have been killed. The mortality values thus determined are recalculated using the Colby-formula.

The following combination of compound and biological showed a synergistic effect according to the invention:

TABLE 2-1

| Phaedon cochleariae larvae - Test | | | |
|---|---|---|---|
| Active ingredient/ biological control agent | Concentration g ai/ha | Mortality in % after $2^d$ | |
| Compound (I-3) | 60 g ai/ha | 20 | |
| Bacillus thuringiensis subsp. tenebrionis strain NB 176, spores | 150 g spore preparation/ha ($=1.5 \times 10^9$ spores/ha) | 0 | |
| | | obs.* | cal.** |
| Compound (I-3) + B. thuringiensis subsp. tenebrionis | 60 + 150 | 45 | 20 |

Phaedon cochleariae Larvae—Spray Application

| Solvent: | 78.0 parts by weight of acetone |
| --- | --- |
| | 1.5 parts by weight of dimethylformamide |
| Emulsifier: | 0.5 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. To produce a suitable preparation of a biological suspension the cells, viruses or spores are diluted with emulsifier-containing water to the desired concentration.

Chinese cabbage (*Brassica pekinesis*) leaf—discs are sprayed with a preparation of the active ingredient of the desired concentration. Once dry, the leaf discs are infested with mustard beetle larvae (*Phaedon cochleariae*).

After the specified period of time, mortality in % is determined. 100% means that all the beetle larvae have been killed; 0% means that none of the beetle larvae have been killed. The mortality values thus determined are recalculated using the Colby-formula.

The following combinations of compound and biological showed a synergistic effect according to the invention:

TABLE 2-2

Phaedon cochleariae larvae - Test

| Active ingredient/ biological control agent | Concentration g ai/ha | Mortality in % after $6^d$ | |
| --- | --- | --- | --- |
| | | obs.* | cal.** |
| Compound (I-3) | 100 g ai/ha | 0 | |
| *Bacillus subtilis* strain GB03 (ATCC SD-1397) | 2000 g spore preparation/ha ($\hat{=}3 \times 10^{12}$ spores/ha) | 0 | |
| Compound (I-3) + *Bacillus subtilis* GB03 | 100 + 2000 | 33 | 0 |
| *Bacillus amyloliquefaciens* strain FZB 42 (DSM 23117) | 2000 g spore preparation/ha ($\hat{=}5 \times 10^{13}$ spores/ha) | 0 | |
| | | obs.* | cal.** |
| Compound (I-3) + *Bacillus amyloliquefaciens* FZB 42 | 100 + 2000 | 50 | 0 |
| *Metschnikowia fructicola* strain NRRL Y-30752, yeast cells | 1000 g spore preparation/ha ($\hat{=}2 \times 10^{13}$ cells/ha) | 0 | |
| | | obs.* | cal.** |
| Compound (I-3) + *Metschnikowia fructicola* | 100 + 1000 | 33 | 0 |
| Cydia pomonella granulosis virus (CpGV) | 1000 g spore preparation/ha | 0 | |
| | | obs.* | cal.** |
| Compound (I-3) + CpGV Virus | 100 + 1000 | 67 | 0 |
| *Metarhizium anisopliae* strain F52 (DSM3884) | 100 g spore preparation/ha ($\hat{=}9 \times 10^{10}$ spores/ha) | 0 | |
| | | obs.* | cal.** |
| Compound (I-3) + *Metarhizium anisopliae* F52 | 100 + 100 | 67 | 0 |

*obs. = observed insecticidal efficacy,
**cal. = efficacy calculated with Colby-formula Example 3

*Diabrotica balteata* Test/Larvae—Soil Application

| Solvent: | 7 parts by weight of dimethylformamide |
| --- | --- |
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. To produce a suitable preparation of a spore suspension the spores are diluted with emulsifier-containing water to the desired concentration.

The preparation containing the active ingredient is thoroughly mixed into the soil. The stated concentration is based on the amount of active ingredient per unit volume of soil (mg/l=ppm). The treated soil is filled into pots and sown with 5 corn seeds per pot. 3 days after sowing larvae of the Banded Cucumber Beetle (*Diabrotica balteata*) are placed in the soil.

After the desired period of time the level of activity expressed in % is determined. The level of activity is calculated on the basis of the number of corn plants which have successfully germinated. The efficacy values determined thus are recalculated using the Colby-formula.

The following combination of compound and biological showed a synergistic effect according to the invention:

TABLE 3

Diabrotica balteata larvae - Test

| Active ingredient/ biological control agent | Concentration g ai/ha | Efficacy in % after $5^d$ | |
| --- | --- | --- | --- |
| Compound (I-3) | 60 g ai/ha | 75 | |
| *Metarhizium anisopliae* strain F52 (DSM3884) | 2500 g spore preparation/ha ($\hat{=}2.25 \times 10^{12}$ spores) | 0 | |
| | | obs.* | cal.** |
| Compound (I-3) + *Metarhizium anisopliae* F52 | 60 + 2500 | 90 | 75 |

*obs. = observed insecticidal efficacy;
**cal. = efficacy calculated with Colby-formula Example 4

Seed Treatment—Germination Test Soybean

Seeds of soybean (*Glycine max*) were treated by being mixed with the desired amount of active compound and spores and water. After drying, 25 seeds were sown into each pot filled with sandy loam.

After 4 days the level of activity expressed in % was determined. The level of activity was calculated on the basis of the number of soybean plants which have successfully germinated.

The following combination of compound and biological showed a superior germination effect compared to the single treatments and control:

| Active ingredient/ biological control agent | Concentration g ai/kg seeds | Germination in % related to untreated control Evaluation after 4$^d$ |
|---|---|---|
| Control (seeds without treatment) | | 100 |
| Compound (I-3) | 0.3 g ai/ha | 72.73 |
| *Bacillus amyloliquefaciens* strain FZB 42 (DSM23117) | 0.15 g spore preparation/ha (=3.75 × 10$^9$ spores) | 90.91 |
| Compound (I-3) + *Bacillus amyloliquefaciens* FZB 42 | 0.3 + 0.15 | 105.45 |

The invention claimed is:

1. A combination for reducing overall damage of a plant and/or a plant part and loss in harvested fruits or vegetables caused by an insect, a mite, a nematode and/or a phytopathogen comprising an enaminocarbonyl compound of formula (I-3)

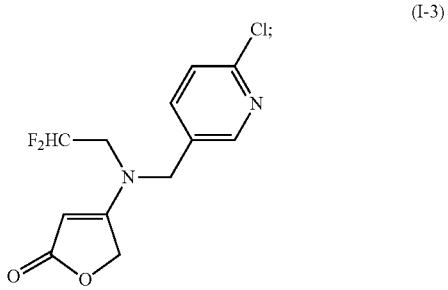 [SMILES: O=C1C=C(N(Cc2ccc(Cl)nc2)CC(F)F)CO1]

and at least one biological control agent selected from the group consisting of Bacillus subtilis, Bacillus thuringiensis, Bacillus amyloliquefaciens, Metarhizium anisopliae, Paecilomyces lilacinus, Metschnikowia fructicola, and Cydia pomonella granulosis virus.

2. A method for reducing overall damage of a plant and/or a plant part and loss in harvested fruits or vegetables caused by an insect, a mite, a nematode and/or a phytopathogen comprising simultaneously and/or sequentially applying to a plant, a plant part, a harvested fruit and/or a vegetable an enaminocarbonyl compound of formula (I-3)

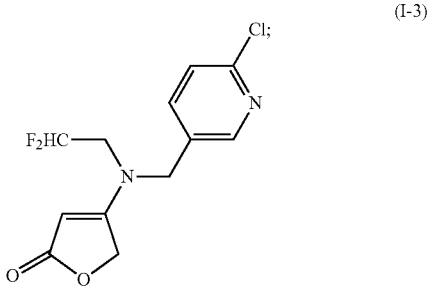 [SMILES: O=C1C=C(N(Cc2ccc(Cl)nc2)CC(F)F)CO1]

and at least one biological control agent selected from the group consisting of Bacillus subtilis, Bacillus thuringiensis, Bacillus amyloliquefaciens, Metarhizium anisopliae, Paecilomyces lilacinus, Metschnikowia fructicola, and Cydia pomonella granulosis virus.

3. The method according to claim 2, further comprising applying an effective amount of inoculant to promote plant health.

4. The method according to claim 2, wherein the enaminocarbonyl compound of formula (I 3) is applied to a plant part that is a seed and/or a plant emerging from a seed.

5. The method according to claim 4, wherein the enaminocarbonyl compound of formula (I-3) is applied to a seed that is from a conventional and/or a transgenic plant.

6. The method according to claim 4, wherein the enaminocarbonyl compound of formula (I-3) is applied to a plant that is a horticultural crop selected from the group consisting of carrots, pumpkin, squash, zucchini, potato, sweet corn, onions, ornamentals, medicinal herbs, culinary herbs, tomatoes, spinach, pepper, melon, lettuce, cucumber, celery, beets, cabbage, cauliflower, broccoli, Brussels sprouts, turnip cabbage, kale, radish, rutabaga, turnip, asparagus, bean, pea, apples, raspberry, strawberry, banana, mango, grapes, peaches, pears, guava, pineapple, a pomegranate, garlic, capsicum, chili, radish, star fruit, tapioca, walnuts, lemon, mandarin, mangold, mushroom, olive, orange, papaya, paprika, passion fruit, peanuts, pecan nuts, prune, pistachio nuts, persimmon, pamplemouse (grapefruit), eggplant, endive, cranberry, gooseberry, hazel nuts, kiwifruit, almonds, amaranth, apricot, artichoke, avocado, blackberry, cashew nut, cherry, clementine, coconut, and cantaloupes.

7. The method according to claim 4, wherein the enaminocarbonyl compound of formula (I-3) is applied to a plant that is a broad acre crop selected from the group consisting of cotton, corn, soybean, cereal, canola, oil seed rape, sugar cane and rice.

8. A formulation comprising a compound of formula (I 3)

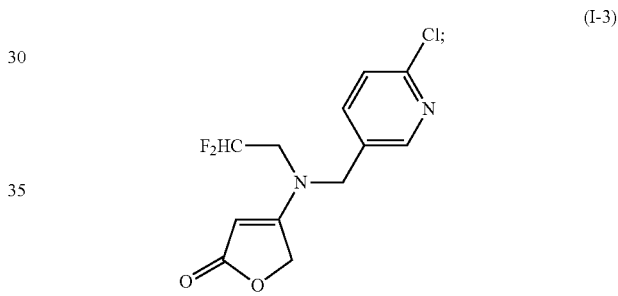

at least one biological control agent selected from the group consisting of Bacillus subtilis, Bacillus thuringiensis, Bacillus amyloliquefaciens, Metarhizium anisopliae, Paecilomyces lilacinus, Metschnikowia fructicola, and Cydia pomonella granulosis virus;
and a carrier and/or additive.

9. The combination according to claim 1, further comprising an effective amount of inoculant to promote plant health.

10. A combination according to claim 1 comprising synergistically effective amounts of an enaminocarbonyl compound of formula (I-3)

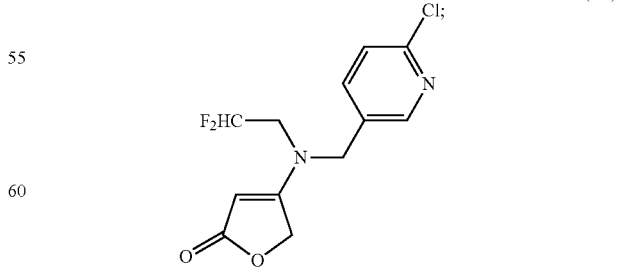

and at least one biological control agent selected from the group consisting of Bacillus subtilis at a weight ratio of the enaminocarbonyl compound to the Bacillus subtilis of between 10:1 and 1:100, Bacillus thuringiensis at a weight ratio of the enaminocarbonyl compound to the Bacillus thuringiensis of between 500:1 and 1:100, Bacillus amyloliquefaciens at a weight ratio of the enaminocarbonyl compound to the Bacillus amyloliquefaciens of between 100:1 and 1:100, Metarhizium anisopliae at a weight ratio of the enaminocarbonyl compound to the Metarhizium anisopliae of between 100:1 and 1:100, Paecilomyces lilacinus at a weight ratio of the enaminocarbonyl compound to the Paecilomyces lilacinus of between 500:1 and 1:500, Metschnikowia fructicola at a weight ratio of the enaminocarbonyl compound to the Metschnikowia fructicola of between 10:1 and 1:100, and Cydia pomonella granulosis virus at a weight ratio of the enaminocarbonyl compound to the virus of between 12:1 and 1:75.

11. The combination according to claim 10, further comprising an effective amount of inoculant to promote plant health.

12. The combination according to claim 10 wherein the biological control agent is Bacillus subtilis.

13. The combination according to claim 10 wherein the biological control agent is Bacillus thuringiensis.

14. The combination according to claim 10 wherein the biological control agent is Bacillus amyloliquefaciens.

15. The combination according to claim 10 wherein the biological control agent is Metarhizium anisopliae.

16. The combination according to claim 10 wherein the biological control agent is Paecilomyces lilacinus.

17. The combination according to claim 10 wherein the biological control agent is Metschnikowia.

18. The combination according to claim 10 wherein the biological control agent is Cydia pomonella granulosis virus.

19. A method according to claim 2 comprising simultaneously and/or sequentially applying to a plant, a plant part, a harvested fruit and/or a vegetable an enaminocarbonyl compound of formula (I-3)

(I-3)

and at least one biological control agent selected from the group consisting of 50 to 5000 g/ha of Bacillus subtilis at a weight ratio of the enaminocarbonyl compound to the Bacillus subtilis of Between 10:1 and 1:100, 0.1 to 5000 g/ha of Bacillus thuringiensis at a weight ratio of the enaminocarbonyl compound to the Bacillus thuringiensis of between 500:1 and 1:100, 500 to 8000 g/ha of Bacillus amyloliquefaciens at a weight ratio of the enaminocarbonyl compound to the Bacillus amyloliquefaciens of between 100:1 and 1:100, 50 to 7500 g/ha of Metarhizium anisopliae at a weight ratio of the enaminocarbonyl compound to the Metarhizium anisopliae of between 100:1 and 1:100, 50 to 7500 g/ha of Paecilomyces lilacinus at a weight ratio of the enaminocarbonyl compound to the Paecilomyces lilacinus of between 500:1 and 1:500, 50 to 5000 g/ha of Metschnikowia fructicola at a weight ratio of the enaminocarbonyl compound to the Metschnikowia fructicola of between 10:1 and 1:100, and 50 to 5000 g/ha of Cydia pomonella granulosis virus at a weight ratio of the enaminocarbonyl compound to the virus of between 12:1 and 1:75.

20. The method according to claim 19, further comprising applying an effective amount of inoculant to promote plant health.

21. A formulation according to claim 8 comprising a compound of formula (I-3)

(I-3)

at least one biological control agent selected from the group consisting of Bacillus subtilis at a weight ratio of the enaminocarbonyl compound to the Bacillus subtilis of between 10:1 and 1:100, Bacillus thuringiensis at a weight ratio of the enaminocarbonyl compound to the Bacillus thuringiensis of between 500:1 and 1:100, Bacillus amyloliquefaciens at a weight ratio of the enaminocarbonyl compound to the Bacillus amyloliquefaciens of between 100:1 and 1:100,Metarhizium anisopliae at a weight ratio of the enaminocarbonyl compound to the Metarhizium anisopliae of between 100:1 and 1:100, Paecilomyces lilacinus at a weight ratio of the enamino-carbonyl compound to the Paecilomyces lilacinus of between 500:1 and 1:500, Metschnikowia fructicola at a weight ratio of the enaminocarbonyl compound to the Metschnikowia fructicola of between 10:1 and 1:100, and Cydia pomonella granulosis virus at a weight ratio of the enaminocarbonyl compound to the virus of between 12:1 and 1:75; and a carrier and/or additive.

* * * * *